(12) United States Patent
Farascioni

(10) Patent No.: US 8,899,461 B2
(45) Date of Patent: Dec. 2, 2014

(54) TISSUE STOP FOR SURGICAL INSTRUMENT

(75) Inventor: David Farascioni, Bethel, CT (US)

(73) Assignee: Covidien LP, Mansfield, MA (US)

( * ) Notice: Subject to any disclaimer, the term of this patent is extended or adjusted under 35 U.S.C. 154(b) by 472 days.

(21) Appl. No.: 13/208,447

(22) Filed: Aug. 12, 2011

(65) Prior Publication Data

US 2012/0080474 A1    Apr. 5, 2012

Related U.S. Application Data

(60) Provisional application No. 61/388,650, filed on Oct. 1, 2010.

(51) Int. Cl.
*A61B 17/064* (2006.01)
*A61B 17/072* (2006.01)
*A61B 17/32* (2006.01)

(52) U.S. Cl.
CPC . *A61B 17/07207* (2013.01); *A61B 2017/07221* (2013.01); *A61B 2017/320052* (2013.01); *A61B 2017/07271* (2013.01)
USPC .................. 227/175.1; 227/176.1; 227/180.1; 606/144; 606/148

(58) Field of Classification Search
CPC ........... A61B 17/07207; A61B 17/072; A61B 17/068
USPC ............. 227/175.1–182.1; 606/139, 142–15, 606/147–149
See application file for complete search history.

(56) References Cited

U.S. PATENT DOCUMENTS

| | | | |
|---|---|---|---|
| 3,017,637 A | 1/1962 | Sampson |
| 3,079,606 A | 3/1963 | Bobrov et al. |
| 3,490,675 A | 1/1970 | Green et al. |
| 3,499,591 A | 3/1970 | Green |
| 3,777,538 A | 12/1973 | Weatherly et al. |
| 3,882,854 A | 5/1975 | Hulka et al. |

(Continued)

FOREIGN PATENT DOCUMENTS

| | | |
|---|---|---|
| AU | 5476586 | 9/1986 |
| CA | 2 773 414 | 11/2012 |

(Continued)

OTHER PUBLICATIONS

European Search Report dated Aug. 5, 2013 in European Patent Application No. 11250785.

*Primary Examiner* — Stephen F Gerrity
*Assistant Examiner* — Eyamindae Jallow

(57) ABSTRACT

A surgical instrument for surgically joining a tissue is disclosed. The surgical instrument comprises a handle assembly, an elongate portion extending distally from the handle assembly, a pair of opposed jaw members, and a tissue stop. The tissue stop is mechanically engaged with a first jaw member and is configured to retain the tissue between jaw members. The tissue stop is movable between a first position, where a stopping portion of the tissue stop is disposed between a tissue-contacting surface of the first jaw member and a tissue-contacting surface of the second jaw member, and a second position, where the stopping portion is between the tissue-contacting surface of the first jaw member and a lower surface of the first jaw member. A portion of the tissue stop is made of stamped metal section and a portion of the tissue stop is made of an overmolded plastic section.

20 Claims, 11 Drawing Sheets

(56) References Cited

U.S. PATENT DOCUMENTS

| | | | |
|---|---|---|---|
| 4,027,510 | A | 6/1977 | Hiltebrandt |
| 4,086,926 | A | 5/1978 | Green et al. |
| 4,244,372 | A | 1/1981 | Kapitanov et al. |
| 4,429,695 | A | 2/1984 | Green |
| 4,505,414 | A | 3/1985 | Filipi |
| 4,520,817 | A | 6/1985 | Green |
| 4,576,167 | A | 3/1986 | Noiles |
| 4,589,413 | A | 5/1986 | Malyshev et al. |
| 4,596,351 | A | 6/1986 | Fedotov et al. |
| 4,602,634 | A | 7/1986 | Barkley |
| 4,605,001 | A | 8/1986 | Rothfuss et al. |
| 4,608,981 | A | 9/1986 | Rothfuss et al. |
| 4,610,383 | A | 9/1986 | Rothfuss et al. |
| 4,633,861 | A | 1/1987 | Chow et al. |
| 4,633,874 | A | 1/1987 | Chow et al. |
| 4,664,305 | A | 5/1987 | Blake, III et al. |
| 4,671,445 | A | 6/1987 | Barker et al. |
| 4,700,703 | A | 10/1987 | Resnick et al. |
| 4,703,887 | A | 11/1987 | Clanton et al. |
| 4,715,520 | A | 12/1987 | Roehr, Jr. et al. |
| 4,728,020 | A | 3/1988 | Green et al. |
| 4,752,024 | A | 6/1988 | Green et al. |
| 4,784,137 | A | 11/1988 | Kulik et al. |
| 4,819,853 | A | 4/1989 | Green |
| 4,863,088 | A | 9/1989 | Redmond et al. |
| 4,869,415 | A | 9/1989 | Fox |
| 4,881,544 | A | 11/1989 | Green et al. |
| 4,892,244 | A | 1/1990 | Fox et al. |
| 4,924,864 | A | 5/1990 | Danzig |
| 4,955,959 | A | 9/1990 | Tompkins et al. |
| 4,978,049 | A | 12/1990 | Green |
| 4,991,764 | A | 2/1991 | Mericle |
| 5,014,899 | A | 5/1991 | Presty et al. |
| 5,031,814 | A | 7/1991 | Tompkins et al. |
| 5,040,715 | A | 8/1991 | Green et al. |
| 5,065,929 | A | 11/1991 | Schulze et al. |
| 5,071,430 | A | 12/1991 | deSalis et al. |
| 5,074,454 | A | 12/1991 | Peters |
| 5,083,695 | A | 1/1992 | Foslien et al. |
| 5,084,057 | A | 1/1992 | Green et al. |
| 5,104,025 | A | 4/1992 | Main et al. |
| 5,106,008 | A | 4/1992 | Tompkins et al. |
| 5,111,987 | A | 5/1992 | Moeinzadeh et al. |
| 5,129,570 | A | 7/1992 | Schulze et al. |
| 5,141,144 | A | 8/1992 | Foslien et al. |
| 5,156,315 | A | 10/1992 | Green et al. |
| 5,156,614 | A | 10/1992 | Green et al. |
| 5,163,943 | A | 11/1992 | Mohiuddin et al. |
| 5,170,925 | A | 12/1992 | Madden et al. |
| 5,171,247 | A | 12/1992 | Hughetti et al. |
| 5,173,133 | A | 12/1992 | Morin et al. |
| 5,180,092 | A | 1/1993 | Crainich |
| 5,188,274 | A | 2/1993 | Moeinzadeh et al. |
| 5,220,928 | A | 6/1993 | Oddsen et al. |
| 5,221,036 | A | 6/1993 | Takase |
| 5,242,457 | A | 9/1993 | Akopov et al. |
| 5,246,156 | A | 9/1993 | Rothfuss et al. |
| 5,253,793 | A | 10/1993 | Green et al. |
| 5,263,629 | A | 11/1993 | Trumbull et al. |
| RE34,519 | E | 1/1994 | Fox et al. |
| 5,275,323 | A | 1/1994 | Schulze et al. |
| 5,282,807 | A | 2/1994 | Knoepfler |
| 5,289,963 | A | 3/1994 | McGarry et al. |
| 5,307,976 | A | 5/1994 | Olson et al. |
| 5,308,576 | A | 5/1994 | Green et al. |
| 5,312,023 | A | 5/1994 | Green et al. |
| 5,318,221 | A | 6/1994 | Green et al. |
| 5,326,013 | A | 7/1994 | Green et al. |
| 5,328,077 | A | 7/1994 | Lou |
| 5,330,486 | A | 7/1994 | Wilk |
| 5,332,142 | A | 7/1994 | Robinson et al. |
| 5,336,232 | A | 8/1994 | Green et al. |
| 5,344,061 | A | 9/1994 | Crainich |
| 5,352,238 | A | 10/1994 | Green et al. |
| 5,356,064 | A | 10/1994 | Green et al. |
| 5,358,506 | A | 10/1994 | Green et al. |
| 5,364,001 | A | 11/1994 | Bryan |
| 5,364,002 | A | 11/1994 | Green et al. |
| 5,364,003 | A | 11/1994 | Williamson, IV |
| 5,366,133 | A | 11/1994 | Geiste |
| 5,366,477 | A | 11/1994 | LeMarie, III et al. |
| 5,376,095 | A | 12/1994 | Ortiz |
| 5,379,933 | A | 1/1995 | Green et al. |
| 5,381,943 | A | 1/1995 | Allen et al. |
| 5,382,255 | A | 1/1995 | Castro et al. |
| 5,383,880 | A | 1/1995 | Hooven |
| 5,389,098 | A | 2/1995 | Tsuruta et al. |
| 5,395,033 | A | 3/1995 | Byrne et al. |
| 5,395,034 | A | 3/1995 | Allen et al. |
| 5,397,046 | A | 3/1995 | Savage et al. |
| 5,397,324 | A | 3/1995 | Carroll et al. |
| 5,403,312 | A | 4/1995 | Yates et al. |
| 5,405,072 | A | 4/1995 | Zlock et al. |
| 5,407,293 | A | 4/1995 | Crainich |
| 5,413,268 | A | 5/1995 | Green et al. |
| 5,415,334 | A | 5/1995 | Williamson, IV et al. |
| 5,415,335 | A | 5/1995 | Knodell, Jr. |
| 5,417,361 | A | 5/1995 | Williamson, IV |
| 5,423,471 | A | 6/1995 | Mastri et al. |
| 5,425,745 | A | 6/1995 | Green et al. |
| 5,431,322 | A | 7/1995 | Green et al. |
| 5,431,323 | A | 7/1995 | Smith et al. |
| 5,433,721 | A | 7/1995 | Hooven et al. |
| 5,441,193 | A | 8/1995 | Gravener |
| 5,445,304 | A | 8/1995 | Plyley et al. |
| 5,447,265 | A | 9/1995 | Vidal et al. |
| 5,452,837 | A | 9/1995 | Williamson, IV et al. |
| 5,456,401 | A | 10/1995 | Green et al. |
| 5,464,300 | A | 11/1995 | Crainich |
| 5,465,895 | A | 11/1995 | Knodel et al. |
| 5,467,911 | A | 11/1995 | Tsuruta et al. |
| 5,470,007 | A | 11/1995 | Plyley et al. |
| 5,470,008 | A | 11/1995 | Rodak |
| 5,470,010 | A | 11/1995 | Rothfuss et al. |
| 5,472,132 | A | 12/1995 | Savage et al. |
| 5,474,566 | A | 12/1995 | Alesi et al. |
| 5,476,206 | A | 12/1995 | Green et al. |
| 5,478,003 | A | 12/1995 | Green et al. |
| 5,480,089 | A | 1/1996 | Blewett |
| 5,482,197 | A | 1/1996 | Green et al. |
| 5,484,095 | A | 1/1996 | Green et al. |
| 5,484,451 | A | 1/1996 | Akopov et al. |
| 5,485,947 | A | 1/1996 | Olson et al. |
| 5,485,952 | A | 1/1996 | Fontayne |
| 5,486,185 | A | 1/1996 | Freitas et al. |
| 5,487,499 | A | 1/1996 | Sorrentino et al. |
| 5,487,500 | A | 1/1996 | Knodel et al. |
| 5,489,058 | A | 2/1996 | Plyley et al. |
| 5,490,856 | A | 2/1996 | Person et al. |
| 5,497,933 | A | 3/1996 | DeFonzo et al. |
| 5,501,689 | A | 3/1996 | Green et al. |
| 5,505,363 | A | 4/1996 | Green et al. |
| 5,507,426 | A | 4/1996 | Young et al. |
| 5,518,163 | A | 5/1996 | Hooven |
| 5,518,164 | A | 5/1996 | Hooven |
| 5,529,235 | A | 6/1996 | Boiarski et al. |
| 5,531,744 | A | 7/1996 | Nardella et al. |
| 5,535,934 | A | 7/1996 | Boiarski et al. |
| 5,535,935 | A | 7/1996 | Vidal et al. |
| 5,535,937 | A | 7/1996 | Boiarski et al. |
| 5,540,375 | A | 7/1996 | Bolanos et al. |
| 5,542,594 | A | 8/1996 | McKean et al. |
| 5,549,628 | A | 8/1996 | Cooper et al. |
| 5,551,622 | A | 9/1996 | Yoon |
| 5,553,765 | A | 9/1996 | Knodel et al. |
| 5,554,164 | A | 9/1996 | Wilson et al. |
| 5,554,169 | A | 9/1996 | Green et al. |
| 5,560,530 | A | 10/1996 | Bolanos et al. |
| 5,560,532 | A | 10/1996 | DeFonzo et al. |
| 5,562,239 | A | 10/1996 | Boiarski et al. |
| 5,562,241 | A | 10/1996 | Knodel et al. |
| 5,562,682 | A | 10/1996 | Oberlin et al. |
| 5,562,701 | A | 10/1996 | Huitema et al. |
| 5,564,615 | A | 10/1996 | Bishop et al. |

(56) References Cited

U.S. PATENT DOCUMENTS

| | | |
|---|---|---|
| 5,571,116 A | 11/1996 | Bolanos et al. |
| 5,573,169 A | 11/1996 | Green et al. |
| 5,573,543 A | 11/1996 | Akopov et al. |
| 5,575,799 A | 11/1996 | Bolanos et al. |
| 5,575,803 A | 11/1996 | Cooper et al. |
| 5,577,654 A | 11/1996 | Bishop |
| 5,579,107 A | 11/1996 | Wright et al. |
| 5,584,425 A | 12/1996 | Savage et al. |
| 5,586,711 A | 12/1996 | Plyley et al. |
| 5,588,580 A | 12/1996 | Paul et al. |
| 5,588,581 A | 12/1996 | Conlon et al. |
| 5,597,107 A | 1/1997 | Knodel et al. |
| 5,601,224 A | 2/1997 | Bishop et al. |
| 5,601,573 A | 2/1997 | Fogelberg et al. |
| 5,607,095 A | 3/1997 | Smith et al. |
| 5,615,820 A | 4/1997 | Viola |
| 5,618,291 A | 4/1997 | Thompson et al. |
| 5,624,452 A | 4/1997 | Yates |
| 5,626,587 A | 5/1997 | Bishop et al. |
| 5,628,446 A | 5/1997 | Geiste et al. |
| 5,630,539 A | 5/1997 | Plyley et al. |
| 5,630,540 A | 5/1997 | Blewett |
| 5,630,541 A | 5/1997 | Williamson, IV et al. |
| 5,632,432 A | 5/1997 | Schulze et al. |
| 5,634,584 A | 6/1997 | Okorocha et al. |
| 5,636,780 A | 6/1997 | Green et al. |
| 5,645,209 A | 7/1997 | Green et al. |
| 5,647,526 A | 7/1997 | Green et al. |
| 5,651,491 A | 7/1997 | Heaton et al. |
| 5,653,373 A | 8/1997 | Green et al. |
| 5,653,374 A | 8/1997 | Young et al. |
| 5,653,721 A | 8/1997 | Knodel et al. |
| 5,655,698 A | 8/1997 | Yoon |
| 5,657,921 A | 8/1997 | Young et al. |
| 5,658,300 A | 8/1997 | Bito et al. |
| 5,662,258 A | 9/1997 | Knodel et al. |
| 5,662,259 A | 9/1997 | Yoon |
| 5,662,260 A | 9/1997 | Yoon |
| 5,662,662 A | 9/1997 | Bishop et al. |
| 5,662,666 A | 9/1997 | Onuki et al. |
| 5,665,085 A | 9/1997 | Nardella |
| 5,667,517 A | 9/1997 | Hooven |
| 5,669,544 A | 9/1997 | Schulze et al. |
| 5,673,840 A | 10/1997 | Schulze et al. |
| 5,673,841 A | 10/1997 | Schulze et al. |
| 5,673,842 A | 10/1997 | Bittner et al. |
| 5,676,674 A | 10/1997 | Bolanos et al. |
| 5,680,981 A | 10/1997 | Mililli et al. |
| 5,680,982 A | 10/1997 | Schulze et al. |
| 5,680,983 A | 10/1997 | Plyley et al. |
| 5,681,330 A | 10/1997 | Hughett et al. |
| 5,690,269 A | 11/1997 | Bolanos et al. |
| 5,692,668 A | 12/1997 | Schulze et al. |
| 5,697,542 A | 12/1997 | Knodel et al. |
| 5,702,409 A | 12/1997 | Rayburn et al. |
| 5,704,534 A | 1/1998 | Huitema et al. |
| 5,706,997 A | 1/1998 | Green et al. |
| 5,709,334 A | 1/1998 | Sorrentino et al. |
| 5,711,472 A | 1/1998 | Bryan |
| 5,713,505 A | 2/1998 | Huitema |
| 5,715,988 A | 2/1998 | Palmer |
| 5,716,366 A | 2/1998 | Yates |
| 5,718,359 A | 2/1998 | Palmer |
| 5,725,536 A | 3/1998 | Oberlin et al. |
| 5,725,554 A | 3/1998 | Simon et al. |
| 5,728,110 A | 3/1998 | Vidal et al. |
| 5,732,806 A | 3/1998 | Foshee et al. |
| 5,735,848 A | 4/1998 | Yates et al. |
| 5,743,456 A | 4/1998 | Jones et al. |
| 5,749,893 A | 5/1998 | Vidal et al. |
| 5,752,644 A | 5/1998 | Bolanos et al. |
| 5,762,255 A | 6/1998 | Chrisman et al. |
| 5,762,256 A | 6/1998 | Mastri et al. |
| 5,769,303 A | 6/1998 | Knodel et al. |
| 5,769,892 A | 6/1998 | Kingwell |
| 5,772,099 A | 6/1998 | Gravener |
| 5,772,673 A | 6/1998 | Cuny et al. |
| 5,779,130 A | 7/1998 | Alesi et al. |
| 5,779,131 A | 7/1998 | Knodel et al. |
| 5,779,132 A | 7/1998 | Knodel et al. |
| 5,782,396 A | 7/1998 | Mastri et al. |
| 5,782,397 A | 7/1998 | Koukline |
| 5,782,834 A | 7/1998 | Lucey et al. |
| 5,785,232 A | 7/1998 | Vidal et al. |
| 5,794,834 A | 8/1998 | Hamblin et al. |
| 5,797,536 A | 8/1998 | Smith et al. |
| 5,797,537 A | 8/1998 | Oberlin et al. |
| 5,797,538 A | 8/1998 | Heaton et al. |
| 5,800,449 A | 9/1998 | Wales |
| 5,810,811 A | 9/1998 | Yates et al. |
| 5,810,855 A | 9/1998 | Rayburn et al. |
| 5,814,055 A | 9/1998 | Knodel et al. |
| 5,814,057 A | 9/1998 | Oi et al. |
| 5,816,471 A | 10/1998 | Plyley et al. |
| 5,817,109 A | 10/1998 | McGarry et al. |
| 5,820,009 A | 10/1998 | Melling et al. |
| 5,823,066 A | 10/1998 | Huitema et al. |
| 5,826,776 A | 10/1998 | Schulze et al. |
| 5,829,662 A | 11/1998 | Allen et al. |
| 5,833,695 A | 11/1998 | Yoon |
| 5,836,147 A | 11/1998 | Schnipke |
| 5,862,972 A | 1/1999 | Green et al. |
| 5,865,361 A | 2/1999 | Milliman et al. |
| 5,871,135 A | 2/1999 | Williamson, IV et al. |
| 5,873,873 A | 2/1999 | Smith et al. |
| 5,878,938 A | 3/1999 | Bittner et al. |
| 5,893,506 A | 4/1999 | Powell |
| 5,894,979 A | 4/1999 | Powell |
| 5,897,562 A | 4/1999 | Bolanos et al. |
| 5,901,895 A | 5/1999 | Heaton et al. |
| 5,911,352 A | 6/1999 | Racenet et al. |
| 5,911,353 A | 6/1999 | Bolanos et al. |
| 5,918,791 A | 7/1999 | Sorrentino et al. |
| 5,919,198 A | 7/1999 | Graves, Jr. et al. |
| 5,922,001 A | 7/1999 | Yoon |
| 5,931,847 A | 8/1999 | Bittner et al. |
| 5,941,442 A | 8/1999 | Geiste et al. |
| 5,954,259 A | 9/1999 | Viola et al. |
| 5,964,774 A | 10/1999 | McKean et al. |
| 5,980,510 A | 11/1999 | Tsonton et al. |
| 5,984,938 A | 11/1999 | Yoon |
| 5,988,479 A | 11/1999 | Palmer |
| 5,993,465 A | 11/1999 | Shipp et al. |
| 6,004,335 A | 12/1999 | Vaitekunas et al. |
| 6,010,054 A | 1/2000 | Johnson et al. |
| 6,032,849 A | 3/2000 | Mastri et al. |
| 6,045,560 A | 4/2000 | McKean et al. |
| 6,050,472 A | 4/2000 | Shibata |
| 6,063,097 A | 5/2000 | Oi et al. |
| 6,079,606 A | 6/2000 | Milliman et al. |
| 6,099,551 A | 8/2000 | Gabbay |
| 6,109,500 A | 8/2000 | Alli et al. |
| 6,119,913 A | 9/2000 | Adams et al. |
| 6,131,789 A | 10/2000 | Schulze et al. |
| 6,131,790 A | 10/2000 | Piraka |
| 6,155,473 A | 12/2000 | Tompkins et al. |
| 6,174,309 B1 | 1/2001 | Wrublewski et al. |
| 6,197,017 B1 | 3/2001 | Brock et al. |
| 6,202,914 B1 | 3/2001 | Geiste et al. |
| 6,241,139 B1 | 6/2001 | Milliman et al. |
| 6,241,140 B1 | 6/2001 | Adams et al. |
| 6,250,532 B1 | 6/2001 | Green et al. |
| 6,264,086 B1 | 7/2001 | McGuckin, Jr. |
| 6,264,087 B1 | 7/2001 | Whitman |
| 6,269,977 B1 | 8/2001 | Moore |
| 6,279,809 B1 | 8/2001 | Nicolo |
| 6,315,183 B1 | 11/2001 | Piraka |
| 6,315,184 B1 | 11/2001 | Whitman |
| 6,325,810 B1 | 12/2001 | Hamilton et al. |
| 6,330,965 B1 | 12/2001 | Milliman et al. |
| 6,391,038 B2 | 5/2002 | Vargas et al. |
| 6,398,797 B2 | 6/2002 | Bombard et al. |
| 6,436,097 B1 | 8/2002 | Nardella |
| 6,439,446 B1 | 8/2002 | Perry et al. |

(56) References Cited

U.S. PATENT DOCUMENTS

| | | | |
|---|---|---|---|
| 6,443,973 | B1 | 9/2002 | Whitman |
| 6,463,623 | B2 | 10/2002 | Ahn et al. |
| 6,478,804 | B2 | 11/2002 | Vargas et al. |
| 6,488,196 | B1 | 12/2002 | Fenton, Jr. |
| 6,503,257 | B2 | 1/2003 | Grant et al. |
| 6,505,768 | B2 | 1/2003 | Whitman |
| 6,544,274 | B2 | 4/2003 | Danitz et al. |
| 6,554,844 | B2 | 4/2003 | Lee et al. |
| 6,565,554 | B1 | 5/2003 | Niemeyer |
| 6,587,750 | B2 | 7/2003 | Gerbi et al. |
| 6,592,597 | B2 | 7/2003 | Grant et al. |
| 6,594,552 | B1 | 7/2003 | Nowlin et al. |
| 6,601,749 | B2 | 8/2003 | Sullivan et al. |
| 6,602,252 | B2 | 8/2003 | Mollenauer |
| 6,607,540 | B1 | 8/2003 | Shipp |
| 6,612,053 | B2 | 9/2003 | Liao |
| 6,619,529 | B2 | 9/2003 | Green et al. |
| D480,808 | S | 10/2003 | Wells et al. |
| 6,644,532 | B2 | 11/2003 | Green et al. |
| 6,656,193 | B2 | 12/2003 | Grant et al. |
| 6,669,073 | B2 | 12/2003 | Milliman et al. |
| 6,681,978 | B2 | 1/2004 | Geiste et al. |
| 6,698,643 | B2 | 3/2004 | Whitman |
| 6,716,232 | B1 | 4/2004 | Vidal et al. |
| 6,722,552 | B2 | 4/2004 | Fenton, Jr. |
| 6,731,473 | B2 | 5/2004 | Li et al. |
| 6,755,338 | B2 | 6/2004 | Hahnen et al. |
| 6,783,524 | B2 | 8/2004 | Anderson et al. |
| 6,786,382 | B1 | 9/2004 | Hoffman |
| 6,805,273 | B2 | 10/2004 | Bilotti et al. |
| 6,808,262 | B2 | 10/2004 | Chapoy et al. |
| 6,817,509 | B2 | 11/2004 | Geiste et al. |
| 6,830,174 | B2 | 12/2004 | Hillstead et al. |
| 6,835,199 | B2 | 12/2004 | McGuckin, Jr. et al. |
| 6,843,403 | B2 | 1/2005 | Whitman |
| RE38,708 | E | 3/2005 | Bolanos et al. |
| 6,877,647 | B2 | 4/2005 | Green et al. |
| 6,879,880 | B2 | 4/2005 | Nowlin et al. |
| 6,889,116 | B2 | 5/2005 | Jinno |
| 6,905,057 | B2 | 6/2005 | Swayze et al. |
| 6,953,138 | B1 | 10/2005 | Dworak et al. |
| 6,953,139 | B2 | 10/2005 | Milliman et al. |
| 6,959,852 | B2 | 11/2005 | Shelton, IV et al. |
| 6,962,594 | B1 | 11/2005 | Thevenet |
| 6,964,363 | B2 | 11/2005 | Wales et al. |
| 6,978,921 | B2 | 12/2005 | Shelton, IV et al. |
| 6,981,628 | B2 | 1/2006 | Wales |
| 6,986,451 | B1 | 1/2006 | Mastri et al. |
| 6,988,649 | B2 | 1/2006 | Shelton, IV et al. |
| 6,991,627 | B2 | 1/2006 | Madhani et al. |
| 6,994,714 | B2 | 2/2006 | Vargas et al. |
| 7,000,818 | B2 | 2/2006 | Shelton, IV et al. |
| 7,000,819 | B2 | 2/2006 | Swayze et al. |
| 7,032,799 | B2 | 4/2006 | Viola et al. |
| 7,044,352 | B2 | 5/2006 | Shelton, IV et al. |
| 7,044,353 | B2 | 5/2006 | Mastri et al. |
| 7,055,730 | B2 | 6/2006 | Ehrenfels et al. |
| 7,055,731 | B2 | 6/2006 | Shelton, IV et al. |
| 7,059,508 | B2 | 6/2006 | Shelton, IV et al. |
| 7,070,083 | B2 | 7/2006 | Jankowski |
| 7,083,075 | B2 | 8/2006 | Swayze et al. |
| 7,097,089 | B2 | 8/2006 | Marczyk |
| 7,111,769 | B2 | 9/2006 | Wales et al. |
| 7,114,642 | B2 | 10/2006 | Whitman |
| 7,121,446 | B2 | 10/2006 | Arad et al. |
| 7,128,253 | B2 | 10/2006 | Mastri et al. |
| 7,128,254 | B2 | 10/2006 | Shelton, IV et al. |
| 7,134,587 | B2 | 11/2006 | Schwemberger et al. |
| 7,140,527 | B2 | 11/2006 | Ehrenfels et al. |
| 7,140,528 | B2 | 11/2006 | Shelton, IV |
| 7,143,923 | B2 | 12/2006 | Shelton, IV et al. |
| 7,143,924 | B2 | 12/2006 | Scirica et al. |
| 7,143,925 | B2 | 12/2006 | Shelton, IV et al. |
| 7,143,926 | B2 | 12/2006 | Shelton, IV et al. |
| 7,147,138 | B2 | 12/2006 | Shelton, IV |
| 7,147,139 | B2 | 12/2006 | Schwemberger et al. |
| 7,147,140 | B2 | 12/2006 | Wukusick et al. |
| 7,159,750 | B2 | 1/2007 | Racenet et al. |
| 7,172,104 | B2 | 2/2007 | Scirica et al. |
| 7,188,758 | B2 | 3/2007 | Viola et al. |
| 7,204,404 | B2 | 4/2007 | Nguyen et al. |
| 7,207,471 | B2 | 4/2007 | Heinrich et al. |
| 7,207,472 | B2 | 4/2007 | Wukusick et al. |
| 7,210,609 | B2 | 5/2007 | Leiboff et |
| 7,213,736 | B2 | 5/2007 | Wales et al. |
| 7,225,963 | B2 | 6/2007 | Scirica |
| 7,225,964 | B2 | 6/2007 | Mastri et al. |
| 7,238,195 | B2 | 7/2007 | Viola |
| 7,246,734 | B2 | 7/2007 | Shelton, IV |
| 7,258,262 | B2 | 8/2007 | Mastri et al. |
| 7,278,562 | B2 | 10/2007 | Mastri et al. |
| 7,278,563 | B1 | 10/2007 | Green |
| 7,287,682 | B1 | 10/2007 | Ezzat et al. |
| 7,293,685 | B2 | 11/2007 | Ehrenfels et al. |
| 7,296,724 | B2 | 11/2007 | Green et al. |
| 7,296,772 | B2 | 11/2007 | Wang |
| 7,300,444 | B1 | 11/2007 | Nielson et al. |
| 7,303,108 | B2 | 12/2007 | Shelton, IV |
| 7,308,998 | B2 | 12/2007 | Mastri et al. |
| 7,326,232 | B2 | 2/2008 | Viola et al. |
| 7,328,828 | B2 | 2/2008 | Ortiz et al. |
| 7,328,829 | B2 | 2/2008 | Arad et al. |
| 7,334,717 | B2 | 2/2008 | Rethy et al. |
| RE40,237 | E | 4/2008 | Bilotti et al. |
| 7,354,447 | B2 | 4/2008 | Shelton, IV et al. |
| 7,357,287 | B2 | 4/2008 | Shelton, IV et al. |
| 7,364,061 | B2 | 4/2008 | Swayze et al. |
| 7,367,485 | B2 | 5/2008 | Shelton, IV et al. |
| 7,380,695 | B2 | 6/2008 | Doll et al. |
| 7,380,696 | B2 | 6/2008 | Shelton, IV et al. |
| 7,398,907 | B2 | 7/2008 | Racenet et al. |
| 7,399,310 | B2 | 7/2008 | Edoga et al. |
| 7,401,720 | B1 | 7/2008 | Durrani |
| 7,401,721 | B2 | 7/2008 | Holsten et al. |
| 7,404,508 | B2 | 7/2008 | Smith et al. |
| 7,404,509 | B2 | 7/2008 | Ortiz et al. |
| 7,407,074 | B2 | 8/2008 | Ortiz et al. |
| 7,407,075 | B2 | 8/2008 | Holsten et al. |
| 7,407,077 | B2 | 8/2008 | Ortiz et al. |
| 7,407,078 | B2 | 8/2008 | Shelton, IV et al. |
| 7,416,101 | B2 | 8/2008 | Shelton, IV et al. |
| 7,419,080 | B2 | 9/2008 | Smith et al. |
| 7,419,081 | B2 | 9/2008 | Ehrenfels et al. |
| 7,419,495 | B2 | 9/2008 | Menn et al. |
| 7,422,139 | B2 | 9/2008 | Shelton, IV et al. |
| 7,431,189 | B2 | 10/2008 | Shelton, IV et al. |
| 7,431,730 | B2 | 10/2008 | Viola |
| 7,434,715 | B2 | 10/2008 | Shelton, IV et al. |
| 7,434,717 | B2 | 10/2008 | Shelton, IV et al. |
| 7,438,208 | B2 | 10/2008 | Larson |
| 7,438,209 | B1 | 10/2008 | Hess et al. |
| 7,441,684 | B2 | 10/2008 | Shelton, IV et al. |
| 7,441,685 | B1 | 10/2008 | Boudreaux |
| 7,448,525 | B2 | 11/2008 | Shelton, IV et al. |
| 7,451,904 | B2 | 11/2008 | Shelton, IV |
| 7,455,208 | B2 | 11/2008 | Wales et al. |
| 7,455,676 | B2 | 11/2008 | Holsten et al. |
| 7,458,494 | B2 | 12/2008 | Matsutani et al. |
| 7,461,767 | B2 | 12/2008 | Viola et al. |
| 7,462,185 | B1 | 12/2008 | Knodel |
| 7,464,846 | B2 | 12/2008 | Shelton, IV et al. |
| 7,464,848 | B2 | 12/2008 | Green et al. |
| 7,464,849 | B2 | 12/2008 | Shelton, IV et al. |
| 7,467,740 | B2 | 12/2008 | Shelton, IV et al. |
| 7,472,814 | B2 | 1/2009 | Mastri et al. |
| 7,472,815 | B2 | 1/2009 | Shelton, IV et al. |
| 7,472,816 | B2 | 1/2009 | Holsten et al. |
| 7,473,258 | B2 | 1/2009 | Clauson et al. |
| 7,481,347 | B2 | 1/2009 | Roy |
| 7,481,348 | B2 | 1/2009 | Marczyk |
| 7,481,349 | B2 | 1/2009 | Holsten et al. |
| 7,487,899 | B2 | 2/2009 | Shelton, IV et al. |
| 7,490,749 | B2 | 2/2009 | Schall et al. |
| 7,494,039 | B2 | 2/2009 | Racenet et al. |

(56) References Cited

U.S. PATENT DOCUMENTS

| | | | |
|---|---|---|---|
| 7,494,501 B2 * | 2/2009 | Ahlberg et al. ............... 606/207 |
| 7,500,979 B2 | 3/2009 | Hueil et al. |
| 7,503,474 B2 | 3/2009 | Hillstead et al. |
| 7,506,790 B2 | 3/2009 | Shelton, IV |
| 7,510,107 B2 | 3/2009 | Timm et al. |
| 7,513,408 B2 | 4/2009 | Shelton, IV et al. |
| 7,517,356 B2 | 4/2009 | Heinrich |
| 7,537,602 B2 | 5/2009 | Whitman |
| 7,543,729 B2 | 6/2009 | Ivanko |
| 7,543,730 B1 | 6/2009 | Marczyk |
| 7,543,731 B2 | 6/2009 | Green et al. |
| 7,549,563 B2 | 6/2009 | Mather et al. |
| 7,556,185 B2 | 7/2009 | Viola |
| 7,556,186 B2 | 7/2009 | Milliman |
| 7,559,450 B2 | 7/2009 | Wales et al. |
| 7,559,452 B2 * | 7/2009 | Wales et al. ............... 227/176.1 |
| 7,559,453 B2 | 7/2009 | Heinrich et al. |
| 7,559,937 B2 | 7/2009 | de la Torre et al. |
| 7,565,993 B2 | 7/2009 | Milliman et al. |
| 7,568,603 B2 | 8/2009 | Shelton, IV et al. |
| 7,568,604 B2 | 8/2009 | Ehrenfels et al. |
| 7,568,605 B2 | 8/2009 | Kruszynski |
| 7,571,845 B2 | 8/2009 | Viola |
| 7,575,144 B2 | 8/2009 | Ortiz et al. |
| 7,584,880 B2 | 9/2009 | Racenet et al. |
| 7,588,174 B2 | 9/2009 | Holsten et al. |
| 7,588,175 B2 | 9/2009 | Timm et al. |
| 7,588,176 B2 | 9/2009 | Timm et al. |
| 7,588,177 B2 | 9/2009 | Racenet |
| 7,597,229 B2 | 10/2009 | Boudreaux et al. |
| 7,597,230 B2 | 10/2009 | Racenet et al. |
| 7,604,150 B2 | 10/2009 | Boudreaux |
| 7,604,151 B2 | 10/2009 | Hess et al. |
| 7,607,557 B2 | 10/2009 | Shelton, IV et al. |
| 7,611,038 B2 | 11/2009 | Racenet et al. |
| 7,617,961 B2 | 11/2009 | Viola |
| 7,624,902 B2 | 12/2009 | Marczyk et al. |
| 7,624,903 B2 | 12/2009 | Green et al. |
| 7,631,793 B2 | 12/2009 | Rethy et al. |
| 7,631,794 B2 | 12/2009 | Rethy et al. |
| 7,635,073 B2 | 12/2009 | Heinrich |
| 7,635,074 B2 | 12/2009 | Olson et al. |
| 7,635,373 B2 | 12/2009 | Ortiz |
| 7,637,409 B2 | 12/2009 | Marczyk |
| 7,637,410 B2 | 12/2009 | Marczyk |
| 7,641,091 B2 | 1/2010 | Olson et al. |
| 7,641,092 B2 | 1/2010 | Kruszynski et al. |
| 7,641,093 B2 | 1/2010 | Doll et al. |
| 7,641,095 B2 | 1/2010 | Viola |
| 7,644,848 B2 | 1/2010 | Swayze et al. |
| 7,648,055 B2 | 1/2010 | Marczyk |
| 7,651,017 B2 | 1/2010 | Ortiz et al. |
| 7,654,431 B2 | 2/2010 | Hueil et al. |
| 7,658,311 B2 | 2/2010 | Boudreaux |
| 7,658,312 B2 | 2/2010 | Vidal et al. |
| 7,665,646 B2 | 2/2010 | Prommersberger |
| 7,665,647 B2 | 2/2010 | Shelton, IV et al. |
| 7,669,746 B2 | 3/2010 | Shelton, IV |
| 7,670,334 B2 | 3/2010 | Hueil et al. |
| 7,673,780 B2 | 3/2010 | Shelton, IV et al. |
| 7,673,781 B2 | 3/2010 | Swayze et al. |
| 7,673,782 B2 | 3/2010 | Hess et al. |
| 7,673,783 B2 | 3/2010 | Morgan et al. |
| 7,678,121 B1 | 3/2010 | Knodel |
| 7,681,772 B2 | 3/2010 | Green et al. |
| 7,682,367 B2 | 3/2010 | Shah et al. |
| 7,682,368 B1 | 3/2010 | Bombard et al. |
| 7,690,547 B2 | 4/2010 | Racenet et al. |
| 7,694,865 B2 | 4/2010 | Scirica |
| 7,699,205 B2 | 4/2010 | Ivanko |
| 7,721,933 B2 | 5/2010 | Ehrenfels et al. |
| 7,726,538 B2 | 6/2010 | Holsten et al. |
| 7,726,539 B2 | 6/2010 | Holsten et al. |
| 7,731,727 B2 | 6/2010 | Sauer |
| 7,735,704 B2 | 6/2010 | Bilotti |
| 7,740,160 B2 | 6/2010 | Viola |
| 7,744,628 B2 | 6/2010 | Viola |
| 7,757,924 B2 | 7/2010 | Gerbi et al. |
| 7,757,925 B2 | 7/2010 | Viola et al. |
| 7,762,445 B2 | 7/2010 | Heinrich et al. |
| 7,766,207 B2 | 8/2010 | Mather et al. |
| 7,766,209 B2 | 8/2010 | Baxter, III et al. |
| 7,766,210 B2 | 8/2010 | Shelton, IV et al. |
| 7,766,924 B1 | 8/2010 | Bombard et al. |
| 7,766,928 B2 | 8/2010 | Ezzat et al. |
| 7,770,774 B2 | 8/2010 | Mastri et al. |
| 7,770,775 B2 | 8/2010 | Shelton, IV et al. |
| 7,776,060 B2 | 8/2010 | Mooradian et al. |
| 7,780,055 B2 | 8/2010 | Scirica et al. |
| 7,784,662 B2 | 8/2010 | Wales et al. |
| 7,789,283 B2 | 9/2010 | Shah |
| 7,793,812 B2 | 9/2010 | Moore et al. |
| 7,793,814 B2 | 9/2010 | Racenet et al. |
| 7,794,475 B2 | 9/2010 | Hess et al. |
| 7,798,386 B2 | 9/2010 | Schall et al. |
| 7,799,039 B2 | 9/2010 | Shelton, IV et al. |
| 7,810,690 B2 | 10/2010 | Bilotti et al. |
| 7,810,692 B2 | 10/2010 | Hall et al. |
| 7,810,693 B2 | 10/2010 | Broehl et al. |
| 7,815,091 B2 | 10/2010 | Marczyk |
| 7,815,092 B2 | 10/2010 | Whitman et al. |
| 7,819,296 B2 | 10/2010 | Hueil et al. |
| 7,819,297 B2 | 10/2010 | Doll et al. |
| 7,819,298 B2 | 10/2010 | Hall et al. |
| 7,819,299 B2 | 10/2010 | Shelton, IV et al. |
| 7,823,760 B2 | 11/2010 | Zemlok et al. |
| 7,824,426 B2 | 11/2010 | Racenet et al. |
| 7,828,186 B2 | 11/2010 | Wales |
| 7,828,187 B2 | 11/2010 | Green et al. |
| 7,828,188 B2 | 11/2010 | Jankowski |
| 7,828,189 B2 | 11/2010 | Holsten et al. |
| 7,832,408 B2 | 11/2010 | Shelton, IV et al. |
| 7,832,612 B2 | 11/2010 | Baxter, III et al. |
| 7,837,079 B2 | 11/2010 | Holsten et al. |
| 7,837,081 B2 | 11/2010 | Holsten et al. |
| 7,841,503 B2 | 11/2010 | Sonnenschein et al. |
| 7,845,533 B2 | 12/2010 | Marczyk et al. |
| 7,845,534 B2 | 12/2010 | Viola et al. |
| 7,845,535 B2 | 12/2010 | Scircia |
| 7,845,537 B2 | 12/2010 | Shelton, IV et al. |
| 7,845,538 B2 | 12/2010 | Whitman |
| 7,850,703 B2 | 12/2010 | Bombard et al. |
| 7,857,183 B2 | 12/2010 | Shelton, IV |
| 7,857,184 B2 | 12/2010 | Viola |
| 7,857,185 B2 | 12/2010 | Swayze et al. |
| 7,857,186 B2 | 12/2010 | Baxter, III et al. |
| 7,861,906 B2 | 1/2011 | Doll et al. |
| 7,861,907 B2 | 1/2011 | Green et al. |
| 7,866,524 B2 | 1/2011 | Krehel |
| 7,866,525 B2 | 1/2011 | Scirica |
| 7,866,527 B2 | 1/2011 | Hall et al. |
| 7,866,528 B2 | 1/2011 | Olson et al. |
| 7,870,989 B2 | 1/2011 | Viola et al. |
| 7,886,952 B2 | 2/2011 | Scirica et al. |
| 7,886,953 B2 | 2/2011 | Schwemberger et al. |
| 7,891,532 B2 | 2/2011 | Mastri et al. |
| 7,891,533 B2 | 2/2011 | Green et al. |
| 7,891,534 B2 | 2/2011 | Wenchell et al. |
| 7,896,214 B2 | 3/2011 | Farascioni |
| 7,900,805 B2 | 3/2011 | Shelton, IV et al. |
| 7,901,416 B2 | 3/2011 | Nolan et al. |
| 7,905,380 B2 | 3/2011 | Shelton, IV et al. |
| 7,905,381 B2 | 3/2011 | Baxter, III et al. |
| 7,909,039 B2 | 3/2011 | Hur |
| 7,909,220 B2 | 3/2011 | Viola |
| 7,909,221 B2 | 3/2011 | Viola et al. |
| 7,909,224 B2 | 3/2011 | Prommersberger |
| 7,913,891 B2 | 3/2011 | Doll et al. |
| 7,913,893 B2 | 3/2011 | Mastri et al. |
| 7,914,543 B2 | 3/2011 | Roth et al. |
| 7,918,230 B2 | 4/2011 | Whitman et al. |
| 7,918,276 B2 | 4/2011 | Guignard et al. |
| 7,922,061 B2 | 4/2011 | Shelton, IV et al. |
| 7,922,063 B2 | 4/2011 | Zemlok et al. |

(56) References Cited

U.S. PATENT DOCUMENTS

| | | |
|---|---|---|
| 7,926,691 B2 | 4/2011 | Viola et al. |
| 7,926,692 B2 | 4/2011 | Racenet et al. |
| 7,934,628 B2 | 5/2011 | Wenchell et al. |
| 7,934,630 B2 | 5/2011 | Shelton, IV et al. |
| 7,934,631 B2 | 5/2011 | Balbierz et al. |
| 7,942,300 B2 | 5/2011 | Rethy et al. |
| 7,950,560 B2 | 5/2011 | Zemlok et al. |
| 7,950,561 B2 | 5/2011 | Aranyi |
| 7,950,562 B2 | 5/2011 | Beardsley et al. |
| 7,954,682 B2 | 6/2011 | Giordano et al. |
| 7,954,683 B1 | 6/2011 | Knodel et al. |
| 7,954,684 B2 | 6/2011 | Boudreaux |
| 7,954,685 B2 | 6/2011 | Viola |
| 7,954,686 B2 | 6/2011 | Baxter, III et al. |
| 7,954,687 B2 | 6/2011 | Zemlok et al. |
| 7,959,051 B2 | 6/2011 | Smith et al. |
| 7,963,431 B2 | 6/2011 | Scirica |
| 7,963,432 B2 | 6/2011 | Knodel et al. |
| 7,963,433 B2 | 6/2011 | Whitman et al. |
| 7,967,178 B2 | 6/2011 | Scirica et al. |
| 7,967,179 B2 | 6/2011 | Olson et al. |
| 7,967,180 B2 | 6/2011 | Scirica et al. |
| 7,980,443 B2 | 7/2011 | Scheib et al. |
| 7,988,026 B2 | 8/2011 | Knodel et al. |
| 7,988,027 B2 | 8/2011 | Olson et al. |
| 7,988,028 B2 | 8/2011 | Farascioni et al. |
| 7,992,758 B2 | 8/2011 | Whitman et al. |
| 7,997,468 B2 | 8/2011 | Farascioni |
| 7,997,469 B2 | 8/2011 | Olson et al. |
| 8,002,795 B2 | 8/2011 | Beetel |
| 8,006,885 B2 | 8/2011 | Marczyk |
| 8,006,887 B2 | 8/2011 | Marczyk |
| 8,007,505 B2 | 8/2011 | Weller et al. |
| 8,007,513 B2 | 8/2011 | Nalagatla et al. |
| 8,011,550 B2 | 9/2011 | Aranyi et al. |
| 8,011,551 B2 | 9/2011 | Marczyk et al. |
| 8,011,552 B2 | 9/2011 | Ivanko |
| 8,011,553 B2 | 9/2011 | Mastri et al. |
| 8,011,555 B2 | 9/2011 | Tarinelli et al. |
| 8,012,170 B2 | 9/2011 | Whitman et al. |
| 8,015,976 B2 | 9/2011 | Shah |
| 8,016,177 B2 | 9/2011 | Bettuchi et al. |
| 8,020,742 B2 | 9/2011 | Marczyk |
| 8,028,882 B2 | 10/2011 | Viola |
| 8,028,883 B2 | 10/2011 | Stopek |
| 8,033,438 B2 | 10/2011 | Scirica |
| 8,033,440 B2 | 10/2011 | Wenchell et al. |
| 8,033,441 B2 | 10/2011 | Marczyk |
| 8,033,442 B2 | 10/2011 | Racenet et al. |
| 8,034,077 B2 | 10/2011 | Smith et al. |
| 8,038,044 B2 | 10/2011 | Viola |
| 8,038,045 B2 | 10/2011 | Bettuchi et al. |
| 8,393,516 B2 * | 3/2013 | Kostrzewski ............. 227/180.1 |
| 8,684,254 B2 * | 4/2014 | Kostrzewski ............. 227/180.1 |
| 2004/0007608 A1 | 1/2004 | Ehrenfels et al. |
| 2004/0050902 A1 | 3/2004 | Green |
| 2004/0093029 A1 | 5/2004 | Zubik et al. |
| 2004/0094597 A1 | 5/2004 | Whitman |
| 2004/0108357 A1 | 6/2004 | Milliman |
| 2004/0149802 A1 | 8/2004 | Whitman |
| 2004/0173659 A1 | 9/2004 | Green |
| 2004/0199180 A1 | 10/2004 | Knodel et al. |
| 2004/0199181 A1 | 10/2004 | Knodel et al. |
| 2004/0232199 A1 | 11/2004 | Shelton, IV et al. |
| 2004/0232200 A1 | 11/2004 | Shelton, IV et al. |
| 2004/0232201 A1 | 11/2004 | Wenchell |
| 2004/0243151 A1 | 12/2004 | Demmy |
| 2004/0267310 A1 | 12/2004 | Racenet |
| 2004/0267311 A1 | 12/2004 | Viola et al. |
| 2005/0006429 A1 | 1/2005 | Wales |
| 2005/0006430 A1 | 1/2005 | Wales |
| 2005/0006431 A1 | 1/2005 | Shelton, IV et al. |
| 2005/0006432 A1 | 1/2005 | Racenet |
| 2005/0006433 A1 | 1/2005 | Milliman |
| 2005/0006434 A1 | 1/2005 | Wales et al. |
| 2005/0023324 A1 | 2/2005 | Doll et al. |
| 2005/0023325 A1 | 2/2005 | Gresham |
| 2005/0067457 A1 | 3/2005 | Shelton |
| 2005/0067458 A1 | 3/2005 | Swayze et al. |
| 2005/0067459 A1 | 3/2005 | Swayze et al. |
| 2005/0067460 A1 | 3/2005 | Milliman |
| 2005/0070925 A1 | 3/2005 | Shelton, IV et al. |
| 2005/0070958 A1 | 3/2005 | Swayze et al. |
| 2005/0072827 A1 | 4/2005 | Mollenauer |
| 2005/0082336 A1 | 4/2005 | Ivanko |
| 2005/0101991 A1 * | 5/2005 | Ahlberg et al. ............. 606/205 |
| 2005/0103819 A1 | 5/2005 | Racenet |
| 2005/0119669 A1 | 6/2005 | Demmy |
| 2005/0127131 A1 | 6/2005 | Mastri |
| 2005/0139636 A1 | 6/2005 | Schwemberger et al. |
| 2005/0145671 A1 | 7/2005 | Viola |
| 2005/0145672 A1 | 7/2005 | Schwemberger et al. |
| 2005/0159778 A1 | 7/2005 | Heinrich et al. |
| 2005/0165415 A1 | 7/2005 | Wales |
| 2005/0173490 A1 | 8/2005 | Shelton, IV |
| 2005/0178813 A1 | 8/2005 | Swayze et al. |
| 2005/0184121 A1 | 8/2005 | Heinrich |
| 2005/0184123 A1 | 8/2005 | Scirica et al. |
| 2005/0184124 A1 | 8/2005 | Scirica et al. |
| 2005/0184125 A1 | 8/2005 | Marczyk |
| 2005/0184126 A1 | 8/2005 | Green et al. |
| 2005/0189397 A1 | 9/2005 | Jankowski |
| 2005/0192628 A1 | 9/2005 | Viola |
| 2005/0216055 A1 | 9/2005 | Scirica et al. |
| 2005/0230453 A1 | 10/2005 | Viola |
| 2005/0247752 A1 | 11/2005 | Kelly et al. |
| 2005/0247753 A1 | 11/2005 | Kelly et al. |
| 2005/0263562 A1 | 12/2005 | Shelton, IV et al. |
| 2005/0279804 A1 | 12/2005 | Scirica et al. |
| 2006/0000867 A1 | 1/2006 | Shelton, IV et al. |
| 2006/0000868 A1 | 1/2006 | Shelton, IV et al. |
| 2006/0011699 A1 | 1/2006 | Olson et al. |
| 2006/0016853 A1 | 1/2006 | Racenet |
| 2006/0022014 A1 | 2/2006 | Shelton, IV et al. |
| 2006/0022015 A1 | 2/2006 | Shelton, IV et al. |
| 2006/0025809 A1 | 2/2006 | Shelton, IV |
| 2006/0043147 A1 | 3/2006 | Mastri et al. |
| 2006/0049229 A1 | 3/2006 | Milliman et al. |
| 2006/0049230 A1 | 3/2006 | Shelton, IV et al. |
| 2006/0060630 A1 | 3/2006 | Shelton, IV et al. |
| 2006/0081678 A1 | 4/2006 | Ehrenfels et al. |
| 2006/0097026 A1 | 5/2006 | Shelton, IV |
| 2006/0124688 A1 | 6/2006 | Racenet et al. |
| 2006/0124689 A1 | 6/2006 | Arad et al. |
| 2006/0138193 A1 | 6/2006 | Viola et al. |
| 2006/0138194 A1 | 6/2006 | Viola et al. |
| 2006/0144898 A1 | 7/2006 | Bilotti et al. |
| 2006/0151567 A1 | 7/2006 | Roy |
| 2006/0151568 A1 | 7/2006 | Weller et al. |
| 2006/0151569 A1 | 7/2006 | Ehrenfels et al. |
| 2006/0163312 A1 | 7/2006 | Viola et al. |
| 2006/0175375 A1 | 8/2006 | Shelton, IV et al. |
| 2006/0180634 A1 | 8/2006 | Shelton, IV et al. |
| 2006/0201990 A1 | 9/2006 | Mastri et al. |
| 2006/0201991 A1 | 9/2006 | Mastri et al. |
| 2006/0226195 A1 | 10/2006 | Scirica et al. |
| 2006/0226196 A1 | 10/2006 | Hueil et al. |
| 2006/0255090 A1 | 11/2006 | Milliman et al. |
| 2006/0271038 A1 | 11/2006 | Johnson et al. |
| 2006/0278680 A1 | 12/2006 | Viola et al. |
| 2006/0278681 A1 | 12/2006 | Viola et al. |
| 2006/0289600 A1 | 12/2006 | Wales et al. |
| 2006/0289602 A1 | 12/2006 | Wales et al. |
| 2007/0023477 A1 | 2/2007 | Whitman et al. |
| 2007/0027469 A1 | 2/2007 | Smith et al. |
| 2007/0034669 A1 | 2/2007 | de la Torre et al. |
| 2007/0034670 A1 | 2/2007 | Racenet et al. |
| 2007/0045379 A1 | 3/2007 | Shelton, IV |
| 2007/0045380 A1 | 3/2007 | Mastri et al. |
| 2007/0068989 A1 | 3/2007 | Shelton, IV |
| 2007/0068990 A1 | 3/2007 | Shelton, IV et al. |
| 2007/0073340 A1 | 3/2007 | Shelton, IV et al. |
| 2007/0073341 A1 | 3/2007 | Smith et al. |
| 2007/0075114 A1 | 4/2007 | Shelton, IV et al. |

(56) References Cited

U.S. PATENT DOCUMENTS

| | | |
|---|---|---|
| 2007/0075115 A1 | 4/2007 | Olson et al. |
| 2007/0075116 A1 | 4/2007 | Whitman |
| 2007/0083233 A1 | 4/2007 | Ortiz et al. |
| 2007/0083234 A1 | 4/2007 | Shelton, IV et al. |
| 2007/0084896 A1 | 4/2007 | Doll et al. |
| 2007/0084897 A1 | 4/2007 | Shelton, IV et al. |
| 2007/0084898 A1 | 4/2007 | Scirica |
| 2007/0084899 A1 | 4/2007 | Taylor |
| 2007/0102472 A1 | 5/2007 | Shelton, IV |
| 2007/0102473 A1 | 5/2007 | Shelton, IV |
| 2007/0102474 A1 | 5/2007 | Shelton, IV |
| 2007/0102475 A1 | 5/2007 | Ortiz et al. |
| 2007/0102476 A1 | 5/2007 | Shelton, IV |
| 2007/0106317 A1 | 5/2007 | Shelton, IV |
| 2007/0108252 A1 | 5/2007 | Racenet et al. |
| 2007/0114261 A1 | 5/2007 | Ortiz et al. |
| 2007/0114262 A1 | 5/2007 | Mastri et al. |
| 2007/0119900 A1 | 5/2007 | Ehrenfels et al. |
| 2007/0119901 A1 | 5/2007 | Ehrenfels et al. |
| 2007/0125826 A1 | 6/2007 | Shelton, IV |
| 2007/0125827 A1 | 6/2007 | Viola |
| 2007/0125828 A1 | 6/2007 | Rethy et al. |
| 2007/0145095 A1 | 6/2007 | Heinrich et al. |
| 2007/0145096 A1 | 6/2007 | Viola et al. |
| 2007/0152014 A1 | 7/2007 | Gillum et al. |
| 2007/0158385 A1 | 7/2007 | Hueil et al. |
| 2007/0170225 A1 | 7/2007 | Shelton, IV et al. |
| 2007/0175947 A1 | 8/2007 | Ortiz et al. |
| 2007/0175948 A1 | 8/2007 | Scirica et al. |
| 2007/0175949 A1 | 8/2007 | Shelton, IV et al. |
| 2007/0175950 A1 | 8/2007 | Shelton, IV et al. |
| 2007/0175951 A1 | 8/2007 | Shelton, IV et al. |
| 2007/0175952 A1 | 8/2007 | Shelton, IV et al. |
| 2007/0175953 A1 | 8/2007 | Shelton, IV et al. |
| 2007/0175954 A1 | 8/2007 | Viola |
| 2007/0175955 A1 | 8/2007 | Shelton, IV et al. |
| 2007/0175956 A1 | 8/2007 | Swayze et al. |
| 2007/0175957 A1 | 8/2007 | Shelton, IV et al. |
| 2007/0175958 A1 | 8/2007 | Shelton, IV et al. |
| 2007/0175959 A1 | 8/2007 | Shelton, IV et al. |
| 2007/0175960 A1 | 8/2007 | Shelton, IV et al. |
| 2007/0175961 A1 | 8/2007 | Shelton, IV et al. |
| 2007/0175962 A1 | 8/2007 | Shelton, IV et al. |
| 2007/0175964 A1 | 8/2007 | Shelton, IV et al. |
| 2007/0179528 A1 | 8/2007 | Soltz et al. |
| 2007/0181631 A1 | 8/2007 | Bilotti et al. |
| 2007/0187453 A1 | 8/2007 | Smith et al. |
| 2007/0187454 A1 | 8/2007 | Scirica |
| 2007/0187455 A1 | 8/2007 | Demmy et al. |
| 2007/0194079 A1 | 8/2007 | Hueil et al. |
| 2007/0194080 A1 | 8/2007 | Swayze et al. |
| 2007/0194081 A1 | 8/2007 | Hueil et al. |
| 2007/0194082 A1 | 8/2007 | Morgan et al. |
| 2007/0219563 A1 | 9/2007 | Voegele |
| 2007/0221700 A1 | 9/2007 | Ortiz et al. |
| 2007/0221701 A1 | 9/2007 | Ortiz et al. |
| 2007/0278277 A1 | 12/2007 | Wixey et al. |
| 2007/0295780 A1 | 12/2007 | Shelton et al. |
| 2008/0029570 A1 | 2/2008 | Shelton et al. |
| 2008/0029571 A1 | 2/2008 | Shelton et al. |
| 2008/0029572 A1 | 2/2008 | Shelton et al. |
| 2008/0029573 A1 | 2/2008 | Shelton et al. |
| 2008/0029574 A1 | 2/2008 | Shelton et al. |
| 2008/0029575 A1 | 2/2008 | Shelton et al. |
| 2008/0029576 A1 | 2/2008 | Shelton et al. |
| 2008/0029577 A1 | 2/2008 | Shelton et al. |
| 2008/0048002 A1 | 2/2008 | Smith et al. |
| 2008/0078800 A1 | 4/2008 | Hess et al. |
| 2008/0078801 A1 | 4/2008 | Shelton et al. |
| 2008/0078802 A1 | 4/2008 | Hess et al. |
| 2008/0078803 A1 | 4/2008 | Shelton et al. |
| 2008/0078804 A1 | 4/2008 | Shelton et al. |
| 2008/0078805 A1 | 4/2008 | Omaits et al. |
| 2008/0078806 A1 | 4/2008 | Omaits et al. |
| 2008/0078807 A1 | 4/2008 | Hess et al. |
| 2008/0078808 A1 | 4/2008 | Hess et al. |
| 2008/0110961 A1 | 5/2008 | Voegele et al. |
| 2008/0125812 A1 | 5/2008 | Zubik et al. |
| 2008/1011095 | 5/2008 | McKenna et al. |
| 2008/0149685 A1 | 6/2008 | Smith et al. |
| 2008/0164296 A1 | 7/2008 | Shelton et al. |
| 2008/0169327 A1 | 7/2008 | Shelton et al. |
| 2008/0169328 A1 | 7/2008 | Shelton |
| 2008/0169329 A1 | 7/2008 | Shelton et al. |
| 2008/0169330 A1 | 7/2008 | Shelton et al. |
| 2008/0169331 A1 | 7/2008 | Shelton et al. |
| 2008/0169332 A1 | 7/2008 | Shelton et al. |
| 2008/0169333 A1 | 7/2008 | Shelton et al. |
| 2008/0210738 A1 | 9/2008 | Shelton et al. |
| 2008/0237296 A1 | 10/2008 | Boudreaux et al. |
| 2008/0237298 A1 | 10/2008 | Schall et al. |
| 2008/0277447 A1 | 11/2008 | Smith et al. |
| 2008/0283570 A1 | 11/2008 | Boyden et al. |
| 2008/0283571 A1 | 11/2008 | Boyden et al. |
| 2008/0283572 A1 | 11/2008 | Boyden et al. |
| 2008/0283574 A1 | 11/2008 | Boyden et al. |
| 2008/0283576 A1 | 11/2008 | Boyden et al. |
| 2008/0283577 A1 | 11/2008 | Boyden et al. |
| 2008/0287987 A1 | 11/2008 | Boyden et al. |
| 2008/0296343 A1 | 12/2008 | Schall et al. |
| 2008/0296344 A1 | 12/2008 | Cropper et al. |
| 2008/0296345 A1 | 12/2008 | Shelton, IV et al. |
| 2008/0296346 A1 | 12/2008 | Shelton, IV et al. |
| 2008/0296347 A1 | 12/2008 | Shelton, IV et al. |
| 2008/0302854 A1 | 12/2008 | Rethy et al. |
| 2008/0308601 A1 | 12/2008 | Timm et al. |
| 2008/0308602 A1 | 12/2008 | Timm et al. |
| 2008/0308603 A1 | 12/2008 | Shelton, IV et al. |
| 2008/0308604 A1 | 12/2008 | Timm et al. |
| 2008/0308606 A1 | 12/2008 | Timm et al. |
| 2008/0308607 A1 | 12/2008 | Timm et al. |
| 2008/0314954 A1 | 12/2008 | Boudreaux |
| 2008/0314955 A1 | 12/2008 | Boudreaux et al. |
| 2008/0314957 A1 | 12/2008 | Boudreaux |
| 2008/0314961 A1 | 12/2008 | Boudreaux et al. |
| 2008/0314962 A1 | 12/2008 | Boudreaux |
| 2009/0001121 A1 | 1/2009 | Hess et al. |
| 2009/0001123 A1 | 1/2009 | Morgan et al. |
| 2009/0001124 A1 | 1/2009 | Hess et al. |
| 2009/0001125 A1 | 1/2009 | Hess et al. |
| 2009/0001126 A1 | 1/2009 | Hess et al. |
| 2009/0001130 A1 | 1/2009 | Hess et al. |
| 2009/0005808 A1 | 1/2009 | Hess et al. |
| 2009/0008424 A1 | 1/2009 | Green |
| 2009/0050671 A1 | 2/2009 | Racenet et al. |
| 2009/0057370 A1 | 3/2009 | Marczyk et al. |
| 2009/0065549 A1 | 3/2009 | Viola |
| 2009/0065550 A1 | 3/2009 | Green et al. |
| 2009/0065551 A1 | 3/2009 | Green et al. |
| 2009/0078738 A1 | 3/2009 | Racenet et al. |
| 2009/0078739 A1 | 3/2009 | Viola |
| 2009/0084826 A1 | 4/2009 | Shah et al. |
| 2009/0090763 A1 | 4/2009 | Zemlok et al. |
| 2009/0090764 A1 | 4/2009 | Viola |
| 2009/0090765 A1 | 4/2009 | Blier et al. |
| 2009/0090766 A1 | 4/2009 | Knodel |
| 2009/0095790 A1 | 4/2009 | Whitman et al. |
| 2009/0101692 A1 | 4/2009 | Whitman et al. |
| 2009/0101694 A1 | 4/2009 | Marczyk |
| 2009/0105535 A1 | 4/2009 | Green |
| 2009/0108048 A1 | 4/2009 | Zemlok et al. |
| 2009/0108049 A1 | 4/2009 | Roy |
| 2009/0114699 A1 | 5/2009 | Viola |
| 2009/0114700 A1 | 5/2009 | Marczyk |
| 2009/0114701 A1 | 5/2009 | Zemlok et al. |
| 2009/0131975 A1* | 5/2009 | Ahlberg et al. ............... 606/206 |
| 2009/0134199 A1 | 5/2009 | Heinrich et al. |
| 2009/0209946 A1 | 8/2009 | Swayze et al. |
| 2009/0209990 A1 | 8/2009 | Yates et al. |
| 2009/0218384 A1 | 9/2009 | Aranyi |
| 2009/0236393 A1 | 9/2009 | Viola |
| 2009/0236395 A1 | 9/2009 | Scirica |
| 2009/0242610 A1 | 10/2009 | Shelton, IV et al. |
| 2009/0242611 A1 | 10/2009 | Hathaway et al. |

(56) References Cited

U.S. PATENT DOCUMENTS

| | | |
|---|---|---|
| 2009/0255974 A1 | 10/2009 | Viola |
| 2009/0255975 A1 | 10/2009 | Zemlok et al. |
| 2009/0255976 A1 | 10/2009 | Marczyk et al. |
| 2009/0255977 A1 | 10/2009 | Zemlok |
| 2009/0261142 A1 | 10/2009 | Milliman et al. |
| 2009/0261144 A1 | 10/2009 | Sniffen et al. |
| 2009/0261145 A1 | 10/2009 | Heinrich et al. |
| 2009/0266868 A1 | 10/2009 | Wenchell et al. |
| 2009/0272784 A1 | 11/2009 | Farascioni |
| 2009/0272787 A1 | 11/2009 | Scirica |
| 2009/0277946 A1 | 11/2009 | Marczyk |
| 2009/0277947 A1 | 11/2009 | Viola |
| 2009/0277949 A1 | 11/2009 | Viola et al. |
| 2009/0283568 A1 | 11/2009 | Racenet et al. |
| 2009/0289096 A1 | 11/2009 | Shelton, IV et al. |
| 2009/0302090 A1 | 12/2009 | Shah |
| 2009/0302091 A1 | 12/2009 | Shah |
| 2009/0306708 A1 | 12/2009 | Shah |
| 2009/0308907 A1 | 12/2009 | Nalagatla et al. |
| 2009/0308908 A1 | 12/2009 | Green et al. |
| 2009/0308909 A1 | 12/2009 | Nalagatla et al. |
| 2009/0314820 A1 | 12/2009 | Green et al. |
| 2009/0314821 A1 | 12/2009 | Racenet |
| 2010/0001036 A1 | 1/2010 | Marczyk et al. |
| 2010/0006620 A1 | 1/2010 | Sorrentino et al. |
| 2010/0012702 A1 | 1/2010 | Marczyk |
| 2010/0012703 A1 | 1/2010 | Calabrese et al. |
| 2010/0012704 A1 | 1/2010 | Racenet et al. |
| 2010/0025452 A1 | 2/2010 | Whitman |
| 2010/0032470 A1 | 2/2010 | Hess et al. |
| 2010/0044411 A1 | 2/2010 | Viola |
| 2010/0065605 A1 | 3/2010 | Shelton et al. |
| 2010/0065606 A1 | 3/2010 | Stopek et al. |
| 2010/0065608 A1 | 3/2010 | Olson et al. |
| 2010/0069942 A1 | 3/2010 | Shelton, IV et al. |
| 2010/0072251 A1 | 3/2010 | Baxter, III et al. |
| 2010/0072252 A1 | 3/2010 | Baxter, III et al. |
| 2010/0072253 A1 | 3/2010 | Baxter, III et al. |
| 2010/0072254 A1 | 3/2010 | Aranyi et al. |
| 2010/0072255 A1 | 3/2010 | Olson et al. |
| 2010/0072256 A1 | 3/2010 | Baxter, III et al. |
| 2010/0072258 A1 | 3/2010 | Farascioni et al. |
| 2010/0076429 A1 | 3/2010 | Heinrich |
| 2010/0076459 A1 | 3/2010 | Farascioni |
| 2010/0089970 A1 | 4/2010 | Smith et al. |
| 2010/0089972 A1 | 4/2010 | Marczyk |
| 2010/0089974 A1 | 4/2010 | Shelton, IV |
| 2010/0096432 A1 | 4/2010 | Scirica |
| 2010/0096433 A1 | 4/2010 | Mastri et al. |
| 2010/0096434 A1 | 4/2010 | Viola et al. |
| 2010/0108739 A1 | 5/2010 | Holsten et al. |
| 2010/0116867 A1 | 5/2010 | Balbierz et al. |
| 2010/0116868 A1 | 5/2010 | Prommersberger |
| 2010/0127040 A1 | 5/2010 | Smith et al. |
| 2010/0127041 A1 | 5/2010 | Morgan et al. |
| 2010/0127042 A1 | 5/2010 | Shelton, IV |
| 2010/0127043 A1 | 5/2010 | Olson et al. |
| 2010/0133317 A1 | 6/2010 | Shelton, IV et al. |
| 2010/0133318 A1 | 6/2010 | Boudreaux |
| 2010/0133319 A1 | 6/2010 | Milliman et al. |
| 2010/0133321 A1 | 6/2010 | Racenet et al. |
| 2010/0147921 A1 | 6/2010 | Olson |
| 2010/0147922 A1 | 6/2010 | Olson |
| 2010/0155453 A1 | 6/2010 | Bombard et al. |
| 2010/0163596 A1 | 7/2010 | Marczyk |
| 2010/0163597 A1 | 7/2010 | Shah et al. |
| 2010/0170931 A1 | 7/2010 | Viola |
| 2010/0170933 A1 | 7/2010 | Ivanko |
| 2010/0193566 A1 | 8/2010 | Scheib et al. |
| 2010/0213238 A1 | 8/2010 | Farascioni et al. |
| 2010/0213240 A1* | 8/2010 | Kostrzewski ............... 227/180.1 |
| 2010/0224668 A1 | 9/2010 | Fontayne et al. |
| 2010/0230468 A1 | 9/2010 | Viola |
| 2010/0237130 A1 | 9/2010 | Scirica |
| 2010/0237131 A1 | 9/2010 | Milliman et al. |
| 2010/0237133 A1 | 9/2010 | Shah |
| 2010/0243706 A1 | 9/2010 | Cohen et al. |
| 2010/0243707 A1 | 9/2010 | Olson et al. |
| 2010/0243708 A1 | 9/2010 | Aranyi et al. |
| 2010/0243709 A1 | 9/2010 | Hess et al. |
| 2010/0243710 A1 | 9/2010 | Mastri et al. |
| 2010/0243711 A1 | 9/2010 | Olson et al. |
| 2010/0249802 A1 | 9/2010 | May et al. |
| 2010/0252610 A1 | 10/2010 | Viola |
| 2010/0252611 A1 | 10/2010 | Ezzat et al. |
| 2010/0252612 A1 | 10/2010 | Viola |
| 2010/0264192 A1 | 10/2010 | Marczyk |
| 2010/0264193 A1 | 10/2010 | Huang et al. |
| 2010/0264194 A1 | 10/2010 | Huang et al. |
| 2010/0270356 A1 | 10/2010 | Holsten et al. |
| 2010/0282816 A1 | 11/2010 | Scirica et al. |
| 2010/0282817 A1 | 11/2010 | Ehrenfels et al. |
| 2010/0282819 A1 | 11/2010 | Racenet et al. |
| 2010/0294828 A1 | 11/2010 | Bindra et al. |
| 2010/0294829 A1 | 11/2010 | Giordano et al. |
| 2010/0301095 A1 | 12/2010 | Shelton, IV et al. |
| 2010/0301096 A1 | 12/2010 | Moore et al. |
| 2010/0305552 A1 | 12/2010 | Shelton, IV et al. |
| 2010/0308099 A1 | 12/2010 | Marczyk et al. |
| 2010/0308100 A1 | 12/2010 | Boudreaux |
| 2010/0320252 A1 | 12/2010 | Viola et al. |
| 2010/0320253 A1 | 12/2010 | Marczyk |
| 2010/0320254 A1 | 12/2010 | Zemlok et al. |
| 2011/0006099 A1 | 1/2011 | Hall et al. |
| 2011/0006101 A1 | 1/2011 | Hall et al. |
| 2011/0006103 A1 | 1/2011 | Laurent et al. |
| 2011/0011914 A1 | 1/2011 | Baxter, III et al. |
| 2011/0011915 A1 | 1/2011 | Shelton, IV |
| 2011/0017801 A1 | 1/2011 | Zemlok et al. |
| 2011/0024477 A1 | 2/2011 | Hall |
| 2011/0024478 A1 | 2/2011 | Shelton, IV |
| 2011/0024479 A1 | 2/2011 | Swensgard et al. |
| 2011/0024480 A1 | 2/2011 | Marczyk |
| 2011/0036887 A1 | 2/2011 | Zemlok et al. |
| 2011/0036888 A1 | 2/2011 | Pribanic et al. |
| 2011/0036890 A1 | 2/2011 | Ma |
| 2011/0036891 A1 | 2/2011 | Zemlok et al. |
| 2011/0036892 A1 | 2/2011 | Marczyk et al. |
| 2011/0036893 A1 | 2/2011 | Viola |
| 2011/0036895 A1 | 2/2011 | Marczyk et al. |
| 2011/0042439 A1 | 2/2011 | Johnson et al. |
| 2011/0042440 A1 | 2/2011 | Holsten et al. |
| 2011/0042441 A1 | 2/2011 | Shelton, IV et al. |
| 2011/0062212 A1 | 3/2011 | Shelton, IV et al. |
| 2011/0062213 A1 | 3/2011 | Scirica et al. |
| 2011/0068144 A1 | 3/2011 | Krehel |
| 2011/0068145 A1 | 3/2011 | Bedi et al. |
| 2011/0068146 A1 | 3/2011 | Viola et al. |
| 2011/0068148 A1 | 3/2011 | Hall et al. |
| 2011/0079626 A1 | 4/2011 | Viola et al. |
| 2011/0079628 A1 | 4/2011 | Racenet et al. |
| 2011/0084112 A1 | 4/2011 | Kostrzewski |
| 2011/0084113 A1 | 4/2011 | Bedi et al. |
| 2011/0084114 A1 | 4/2011 | Marczyk et al. |
| 2011/0084115 A1 | 4/2011 | Bedi et al. |
| 2011/0087276 A1 | 4/2011 | Bedi et al. |
| 2011/0089220 A1 | 4/2011 | Ingmanson et al. |
| 2011/0089221 A1 | 4/2011 | Masiakos et al. |
| 2011/0095067 A1 | 4/2011 | Ohdaira |
| 2011/0101066 A1 | 5/2011 | Farascioni et al. |
| 2011/0101067 A1 | 5/2011 | Johnson et al. |
| 2011/0101069 A1 | 5/2011 | Bombard et al. |
| 2011/0101070 A1 | 5/2011 | Bettuchi et al. |
| 2011/0108603 A1 | 5/2011 | Racenet et al. |
| 2011/0108605 A1 | 5/2011 | Sapienza |
| 2011/0108606 A1 | 5/2011 | Whitman |
| 2011/0114702 A1 | 5/2011 | Farascioni |
| 2011/0121049 A1 | 5/2011 | Malinouskas et al. |
| 2011/0121050 A1 | 5/2011 | Nicholas et al. |
| 2011/0121051 A1 | 5/2011 | Shelton, IV et al. |
| 2011/0121052 A1 | 5/2011 | Shelton, IV et al. |
| 2011/0132960 A1 | 6/2011 | Whitman et al. |
| 2011/0132961 A1 | 6/2011 | Whitman et al. |
| 2011/0132962 A1 | 6/2011 | Hall et al. |

(56) References Cited

U.S. PATENT DOCUMENTS

| | | |
|---|---|---|
| 2011/0132963 A1 | 6/2011 | Giordano et al. |
| 2011/0132964 A1 | 6/2011 | Weisenburgh, II et al. |
| 2011/0132965 A1 | 6/2011 | Moore et al. |
| 2011/0139851 A1 | 6/2011 | McCuen |
| 2011/0144640 A1 | 6/2011 | Heinrich et al. |
| 2011/0147433 A1 | 6/2011 | Shelton, IV et al. |
| 2011/0147434 A1 | 6/2011 | Hueil et al. |
| 2011/0155780 A1 | 6/2011 | Boudreaux |
| 2011/0155781 A1 | 6/2011 | Swensgard et al. |
| 2011/0155784 A1 | 6/2011 | Shelton, IV et al. |
| 2011/0155785 A1 | 6/2011 | Laurent et al. |
| 2011/0155786 A1 | 6/2011 | Shelton, IV |
| 2011/0155787 A1 | 6/2011 | Baxter, III et al. |
| 2011/0155788 A1 | 6/2011 | Hillstead et al. |
| 2011/0163146 A1 | 7/2011 | Ortiz et al. |
| 2011/0163147 A1 | 7/2011 | Laurent et al. |
| 2011/0163148 A1 | 7/2011 | Wenchell et al. |
| 2011/0163149 A1 | 7/2011 | Viola |
| 2011/0163150 A1 | 7/2011 | Farascioni |
| 2011/0168756 A1 | 7/2011 | Racenet et al. |
| 2011/0168757 A1 | 7/2011 | Viola et al. |
| 2011/0168758 A1 | 7/2011 | Mastri et al. |
| 2011/0168759 A1 | 7/2011 | Prommersberger |
| 2011/0168760 A1 | 7/2011 | Viola et al. |
| 2011/0174862 A1 | 7/2011 | Shelton, IV et al. |
| 2011/0174863 A1 | 7/2011 | Shelton, IV et al. |
| 2011/0180585 A1 | 7/2011 | Czernik et al. |
| 2011/0180586 A1 | 7/2011 | Shah |
| 2011/0184443 A1 | 7/2011 | Tzakis et al. |
| 2011/0186614 A1 | 8/2011 | Kasvikis |
| 2011/0192881 A1 | 8/2011 | Balbierz et al. |
| 2011/0192882 A1 | 8/2011 | Hess et al. |
| 2011/0192883 A1 | 8/2011 | Whitman et al. |
| 2011/0192884 A1 | 8/2011 | Whitman et al. |
| 2011/0198385 A1 | 8/2011 | Whitman et al. |
| 2011/0198386 A1 | 8/2011 | Viola |
| 2011/0204119 A1 | 8/2011 | McCuen |
| 2011/0204120 A1 | 8/2011 | Crainich |
| 2011/0210157 A1 | 9/2011 | Knodel et al. |
| 2011/0215132 A1 | 9/2011 | Aranyi et al. |
| 2011/0215133 A1 | 9/2011 | Aranyi |
| 2011/0226837 A1 | 9/2011 | Baxter, III et al. |
| 2011/0233258 A1 | 9/2011 | Boudreaux |
| 2011/0233259 A1 | 9/2011 | Olson |
| 2011/0233260 A1 | 9/2011 | Milliman et al. |
| 2011/0240711 A1 | 10/2011 | Scirica |
| 2011/0240712 A1 | 10/2011 | Kostrzewski |
| 2011/0240713 A1 | 10/2011 | Scirica et al. |
| 2011/0240714 A1 | 10/2011 | Whitman et al. |
| 2011/0253765 A1 | 10/2011 | Nicholas et al. |
| 2011/0253766 A1 | 10/2011 | Baxter, III et al. |
| 2011/0257679 A1 | 10/2011 | Ishitsuki et al. |
| 2012/0138660 A1 | 6/2012 | Shelton |
| 2012/0248170 A1* | 10/2012 | Marczyk ................. 227/175.1 |
| 2013/0168433 A1* | 7/2013 | Kostrzewski ............. 227/175.1 |

FOREIGN PATENT DOCUMENTS

| | | |
|---|---|---|
| DE | 2744824 | 4/1978 |
| DE | 2903159 | 1/1980 |
| DE | 3114135 | 10/1982 |
| DE | 4213426 | 10/1992 |
| DE | 4300307 | 7/1994 |
| EP | 0041022 | 12/1981 |
| EP | 0136950 | 4/1985 |
| EP | 0140552 | 5/1985 |
| EP | 0156774 | 10/1985 |
| EP | 0216532 | 4/1987 |
| EP | 0220029 | 4/1987 |
| EP | 0213817 | 11/1987 |
| EP | 0273468 | 7/1988 |
| EP | 0324166 | 7/1989 |
| EP | 0324635 | 7/1989 |
| EP | 0324637 | 7/1989 |
| EP | 0324638 | 7/1989 |
| EP | 0369324 | 5/1990 |
| EP | 0373762 | 6/1990 |
| EP | 0380025 | 8/1990 |
| EP | 0399701 | 11/1990 |
| EP | 0449394 | 10/1991 |
| EP | 0484677 | 5/1992 |
| EP | 0489436 | 6/1992 |
| EP | 0503662 | 9/1992 |
| EP | 0514139 | 11/1992 |
| EP | 0536903 | 4/1993 |
| EP | 0537498 | 4/1993 |
| EP | 0537572 | 4/1993 |
| EP | 0539762 | 5/1993 |
| EP | 0545029 | 6/1993 |
| EP | 0552050 | 7/1993 |
| EP | 0552423 | 7/1993 |
| EP | 0579038 | 1/1994 |
| EP | 0589306 | 3/1994 |
| EP | 0591946 | 4/1994 |
| EP | 0592243 | 4/1994 |
| EP | 0593920 | 4/1994 |
| EP | 0598202 | 5/1994 |
| EP | 0598579 | 5/1994 |
| EP | 0600182 | 6/1994 |
| EP | 0621006 | 10/1994 |
| EP | 0621009 | 10/1994 |
| EP | 0656188 | 6/1995 |
| EP | 0365153 | 8/1995 |
| EP | 0666057 | 8/1995 |
| EP | 0705571 | 4/1996 |
| EP | 0760230 | 3/1997 |
| EP | 1550410 | 7/2005 |
| EP | 2 014 243 | 1/2009 |
| EP | 2 090 253 | 8/2009 |
| EP | 2 090 254 | 8/2009 |
| EP | 2 116 193 | 11/2009 |
| EP | 2 583 630 | 4/2013 |
| EP | 2 580 382 | 5/2013 |
| FR | 2542188 | 9/1984 |
| FR | 2660851 | 10/1991 |
| FR | 2681775 | 10/1991 |
| GB | 1352554 | 4/1971 |
| GB | 1452185 | 10/1976 |
| GB | 1555455 | 11/1979 |
| GB | 2048685 | 12/1980 |
| GB | 2070499 | 9/1981 |
| GB | 2141066 | 12/1984 |
| GB | 2165559 | 4/1986 |
| RU | 980703 | 12/1982 |
| RU | 990220 | 1/1983 |
| SU | 659146 | 4/1979 |
| SU | 728848 | 5/1980 |
| WO | WO83/02247 | 7/1983 |
| WO | WO 89/10094 | 11/1989 |
| WO | WO92/10976 | 7/1992 |
| WO | 9308754 | 5/1993 |
| WO | 9314706 | 8/1993 |
| WO | WO03/022133 | 3/2003 |
| WO | WO 2004/032761 | 4/2004 |

\* cited by examiner

TISSUE STOP FOR SURGICAL INSTRUMENT

CROSS-REFERENCE TO RELATED APPLICATION

This patent application claims priority to, and the benefit of, U.S. Provisional Patent Application Ser. No. 61/388,650, filed on Oct. 1, 2010, the entire contents of which is incorporated herein by reference.

BACKGROUND

1. Technical Field

The present disclosure relates generally to surgical instruments and, more specifically, to surgical instruments for surgically joining tissue.

2. Background of Related Art

Surgical stapling instruments used for applying parallel rows of staples through compressed living tissue are well known in the art. These surgical instruments are commonly employed for closing tissue or organs prior to transaction or resection, for occluding organs in thoracic and abdominal procedures, and for fastening tissue in anastomoses.

Typically, such surgical stapling instruments include an anvil assembly, a cartridge assembly for supporting an array of surgical staples, an approximation mechanism for approximating the anvil and cartridge and anvil assemblies, and a firing mechanism for ejecting the surgical staples from the cartridge assembly.

In use, a surgeon generally initially approximates the anvil and cartridge members. Next, the surgeon can fire the instrument to place staples in tissue. Additionally, the surgeon may use the same instrument or a separate instrument to cut the tissue adjacent or between the row(s) of staples. In certain surgical stapling instruments, the instrument sequentially ejects the staples from the staple cartridge while the anvil and cartridge are approximated. The staples are driven through the tissue and formed against the anvil.

SUMMARY

The present disclosure relates to a surgical instrument for surgically joining a tissue is disclosed. The surgical instrument comprises a handle assembly, an elongate portion, a pair of opposed jaw members, and a tissue stop. The handle assembly includes a movable handle. The elongate portion extends distally from the handle assembly and defines a longitudinal axis. The pair of opposed jaw members are operatively coupled to the elongate portion and extend distally therefrom. The pair of opposed jaw members includes a first jaw member and a second jaw member. The tissue stop is mechanically engaged with the first jaw member and is configured to retain the tissue between the pair of opposed jaw members. The tissue stop is movable between a first position, where a stopping portion of the tissue stop is disposed between a tissue-contacting surface of the first jaw member and a tissue-contacting surface of the second jaw member, and a second position, where the stopping portion is between the tissue-contacting surface of the first jaw member and a lower surface of the first jaw member. A portion of the tissue stop is made of stamped metal section and a portion of the tissue stop is made of an overmolded plastic section.

In disclosed embodiments, the stopping portion of the tissue stop includes a scalloped portion. In disclosed embodiment, the scalloped portion of the tissue stop includes a plurality of spaced-apart semi-circular indents.

In disclosed embodiments, the tissue stop includes a pair of lateral walls. In disclosed embodiments, the stopping portion is disposed on a proximal edge of each lateral wall.

The present disclosure also relates to a loading unit configured for releasable engagement with a surgical instrument. The loading unit comprises a body portion, a pair of jaw members, and a tissue stop. The body portion defines a longitudinal axis and includes a proximal portion configured for releasable engagement with an elongate portion of the surgical instrument. The pair of jaw members extends distally from the body portion. At least one of the jaw members is movable with respect to the other between an open position and an approximated position engaging a body tissue therebetween. The pair of jaw members includes a first jaw member and a second jaw member. The tissue stop is mechanically engaged with the first jaw member and is configured to retain the tissue between the pair of opposed jaw members. The tissue stop is movable between a first position, where a stopping portion of the tissue stop is disposed between a tissue-contacting surface of the first jaw member and a tissue-contacting surface of the second jaw member, and a second position, where the stopping portion is between the tissue-contacting surface of the first jaw member and a lower surface of the first jaw member. A portion of the tissue stop is made of stamped metal section and a portion of the tissue stop is made of an overmolded plastic section.

In disclosed embodiments, the stopping portion of the tissue stop of the loading unit includes a scalloped portion. In disclosed embodiment, the scalloped portion of the tissue stop includes a plurality of spaced-apart semi-circular indents.

In disclosed embodiments, the tissue stop of the loading unit includes a pair of lateral walls. In disclosed embodiments, the stopping portion is disposed on a proximal edge of each lateral wall.

The present disclosure also relates to a tissue stop for use with a surgical instrument. The tissue stop comprises a stamped metal portion and an overmolded plastic portion. The tissue stop is mechanically engaged with a jaw member of the surgical instrument and is configured to retain the tissue between opposed jaw members of the surgical instrument.

In disclosed embodiments, the tissue stop includes a pair of lateral walls. In disclosed embodiments, a stopping portion is disposed on a proximal edge of each lateral wall. In disclosed embodiments, the stopping portion includes a scalloped portion. In disclosed embodiments, the scalloped portion of the tissue stop includes a plurality of spaced-apart semi-circular indents.

BRIEF DESCRIPTION OF FIGURES

Various embodiments of the presently disclosed surgical instrument are disclosed herein with reference to the drawings, wherein.

DETAILED DESCRIPTION

Figure 1:
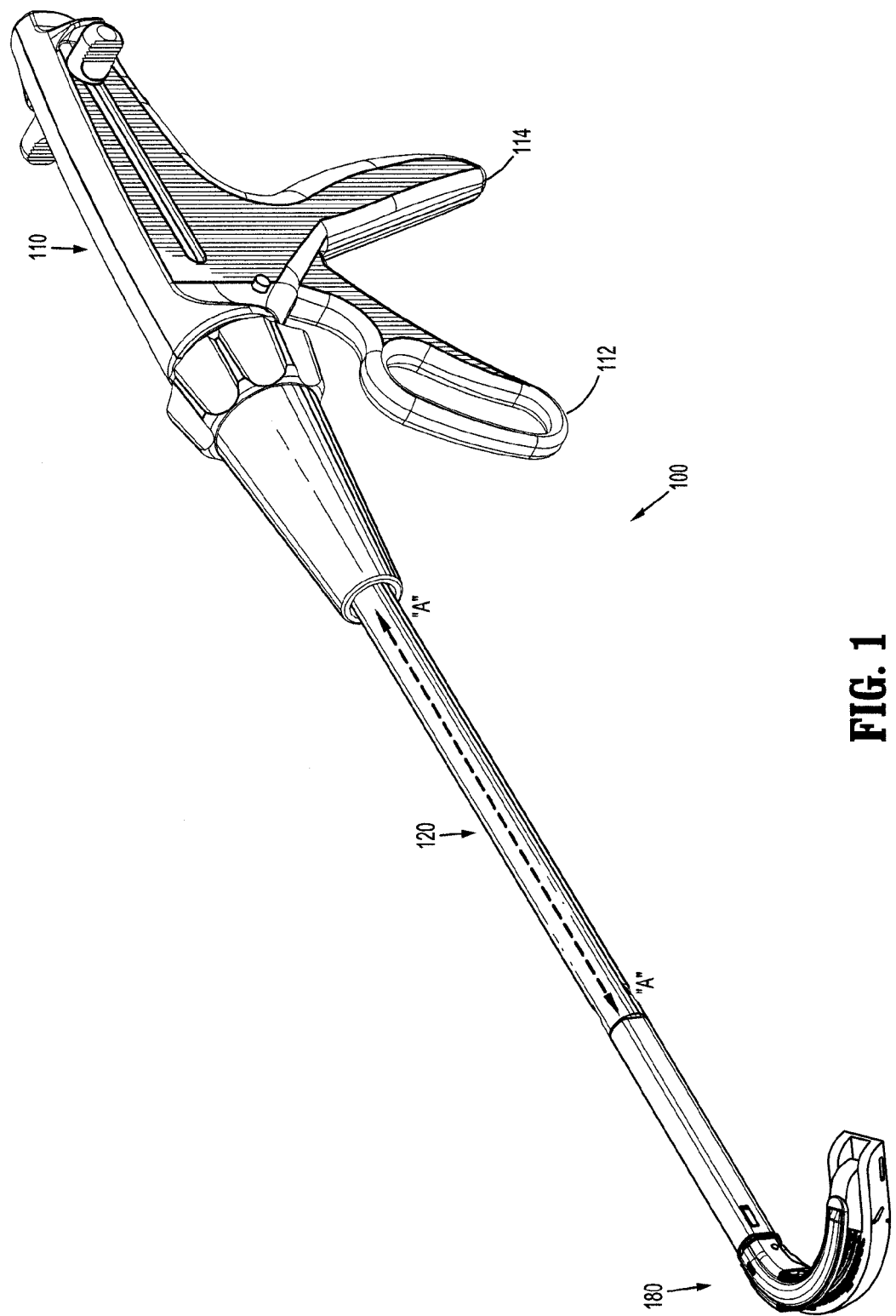
FIG. 1 is a perspective view of a surgical instrument in accordance with the present disclosure.

Embodiments of the presently disclosed surgical instrument are described in detail with reference to the drawings, wherein like reference numerals designate similar or identical elements in each of the several views. In the drawings and the description that follows, the term "proximal" refers to the end of the surgical instrument that is closest to the operator, whereas the term "distal" refers to the end of the surgical instrument that is farthest from the operator.

As appreciated by one skilled in the art, the depicted surgical instrument fires staples, but it may be adapted to fire any other suitable fastener such as clips and two-part fasteners. Additionally, the disclosed tissue stop may be used with an electrosurgical forceps. Further details of electrosurgical forceps are described in commonly-owned patent application Ser. No. 10/369,894, filed on Feb. 20, 2003, entitled VESSEL SEALER AND DIVIDER AND METHOD OF MANUFACTURING THE SAME, the entire contents of which are hereby incorporated by reference herein.

With reference to FIG. 1, reference numeral 100 designates an embodiment of the presently disclosed surgical instrument. In the interest of brevity, the present disclosure focuses on an end effector and a tissue stop of surgical instrument 100. U.S. Patent Applications Publication Nos. 2008/0105730, filed on Nov. 28, 2007; 2008/0110960, filed on Jan. 8, 2008; 2008/0142565, filed on Jan. 24, 2008; 2008/0041916, filed on Oct. 15, 2007; and Ser. No. 11/786,198, filed on Apr. 10, 2007, the disclosures of which are hereby incorporated by reference herein in their entirety, describe in detail the structure and operation of other surgical fastening assemblies.

Figure 2:
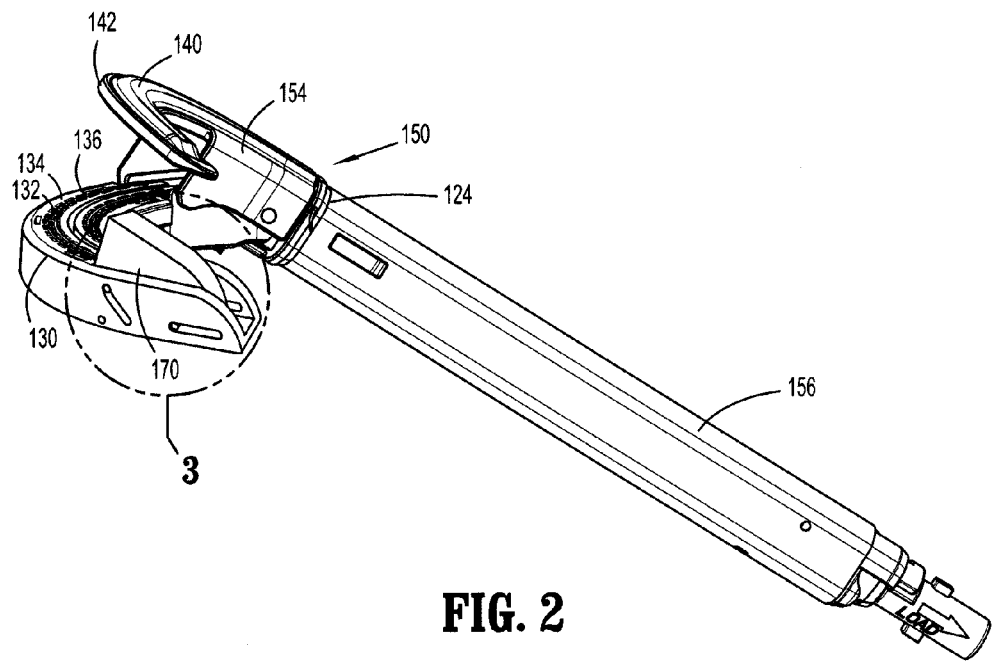
FIG. 2 is a perspective view of a loading unit of the surgical instrument of FIG. 1.

Surgical instrument 100 disclosed in the illustrated embodiments is configured to clamp, fasten, and/or cut tissue. In general, surgical instrument 100 includes a handle assembly 110, an elongate portion 120 extending distally from handle assembly 110 and defining a longitudinal axis "A-A," and a loading unit 180 (collectively referring to a single use loading unit ("SULU") and a disposable loading unit ("DLU")), as shown in FIG. 1. With reference to FIG. 2, loading unit 180 includes a proximal body portion 156, and a tool assembly 150. Proximal body portion 156 is configured to releasably attach to elongate portion 120 of surgical instrument 100 using a variety of attachment features, such as, for example, a bayonet coupling, latch, detent or snap-fit. In other embodiments, the instrument has jaws that are permanently attached to the elongate portion, and a replaceable cartridge, such as a staple cartridge, can be loaded, removed and reloaded in one of the jaws.

Tool assembly 150 includes end effector 154 and a tissue stop 170. End effector 154, which is disposed adjacent distal portion 124 of body portion 156, includes a first jaw member 130 and a second jaw member 140. As shown in FIGS. 1 and 2, each of first and second jaw members 130, 140 is longitudinally curved with respect to the longitudinal axis "A-A." The curved jaw members, as compared to straight jaw members, may help facilitate access to lower pelvic regions, e.g., during lower anterior resection ("LAR"). Additionally, the inclusion of curved jaw members may allow increased visualization to a surgical site and may also allow more room for a surgeon to manipulate target tissue or the jaw members themselves with his or her hand. While the illustrated embodiment depict the jaw members as being curved, it is envisioned and within the scope of the present disclosure that the tissue stop 170 may be used with linear jaw members.

At least one of the jaw members 130, 140 is adapted to move relative to the other jaw member (130 or 140) between spaced and approximated positions. In the illustrated embodiment, first jaw member 130 contains a cartridge assembly 132, and second jaw member 140 includes an anvil assembly 142. Cartridge assembly 132 moves with respect to anvil assembly 142 between spaced and approximated positions upon actuation of a movable handle 112, for example. While cartridge assembly 132 is shown as pivotally movable with respect to anvil assembly 142, anvil assembly 142 may be pivotally mounted with respect to the cartridge assembly 132.

Handle assembly 110 includes a stationary handle 114 and movable handle 112. Movable handle 112 is adapted to move pivotally towards or away from stationary handle 114. Further, movable handle 112 is operatively connected to anvil assembly 142 through a mechanism adapted to convert at least a partial actuation of movable handle 112 into a pivoting motion of at least one of cartridge assembly 132 and anvil assembly 142 between spaced and approximated positions. As recognized by one skilled in the art, any conventional actuation mechanism may be employed to operatively couple movable handle 112 to tool assembly 150.

With reference to FIG. 2, cartridge assembly 132 has a tissue-contacting surface 134 and a plurality of fastener retaining slots 136. Tissue-contacting surface 134 generally faces anvil assembly 142 and, during operation, engages tissue when the anvil assembly 142 is approximated with cartridge assembly 132. Fastener retaining slots 136 are arranged in rows along tissue contacting surface 134 and each fastener retaining slot 136 is adapted to releasably hold a fastener (not shown). For example, when movable handle 112 is pivoted toward stationary handle 114, the fasteners are ejected from fastener retaining slots 136 and move towards anvil assembly 142.

Cartridge assembly 132 also includes a knife channel 138 (FIG. 3) adapted to slidably receive a knife (not shown) or any other suitable cutting tool. Knife channel 138 is defined in the staple cartridge, is disposed between rows of fastener retaining slots 136, and extends along tissue-contacting surface 134. In operation, the knife slides through the knife channel 138 when movable handle 112 pivots towards stationary handle 114. Alternatively, other mechanisms can be used to drive the knife through knife channel 138.

In disclosed embodiments, handle assembly 110 contains an actuation mechanism for deploying the fasteners from fastener retaining slots 136 and advancing a knife along knife channel 138. This actuation mechanism includes a firing rod (not shown) operatively connected to movable handle 112. In operation, pivoting movable handle 112 toward stationary handle 114 causes firing rod to advance distally. Firing rod is in turn operatively coupled to an axial drive assembly at least partially positioned within tool assembly 150. Axial drive assembly is configured to move distally in response to a distal translation of firing rod. The axial drive assembly includes a drive beam that incorporates the knife, an upper member, and a lower member. As the upper member of the drive beam engages the anvil assembly and the lower member of the drive beam engages the cartridge assembly, the distal translation of axial drive assembly causes the anvil assembly 142 to pivot toward the cartridge assembly 132. In addition, the axial drive assembly pushes an actuation sled disposed within the cartridge assembly 132 in a distal direction, while the actuation sled translates distally through end effector 154. As the actuation sled advances distally through the cartridge assembly 132, this actuation sled urges the fasteners out of the fastener retaining slots 136. In certain embodiments, axial drive assembly includes a knife or blade mounted on a distal portion thereof. In operation, the drive beam, including the knife, moves through the knife channel 138 when axial drive assembly moves distally through end effector 154. Further details of an endoscopic surgical stapling instrument are described in detail in commonly-owned U.S. Pat. No. 6,953,139 to Milliman et al., the entire contents of which are hereby incorporated by reference herein. However, it is also envisioned that other methods of approximating the jaw members are also usable, including sliding a clamp bar (not shown). Other methods of ejecting the fasteners are contemplated, such as cam bars, are contemplated.

Figure 3:
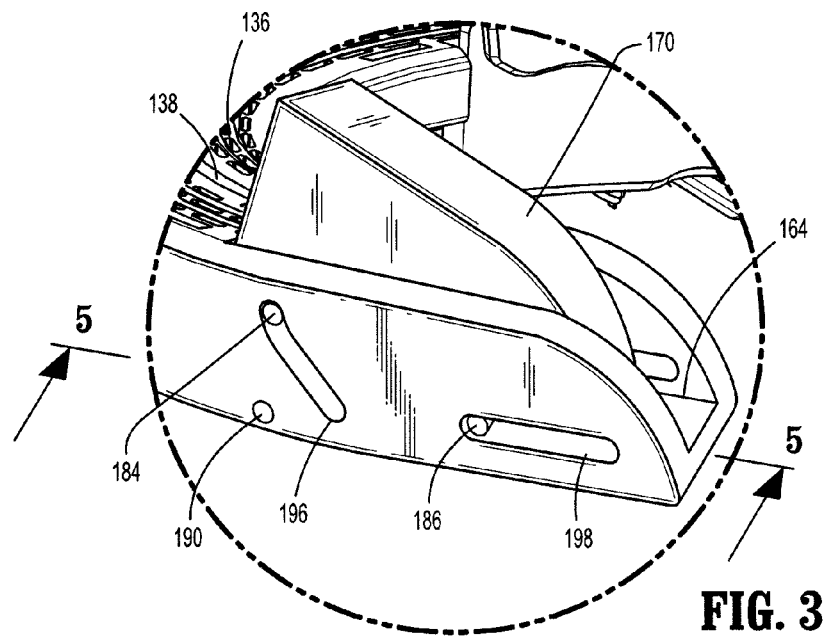
FIG. 3 is a perspective view of the area of detail of FIG. 2 illustrating a tissue stop.
Figure 4:
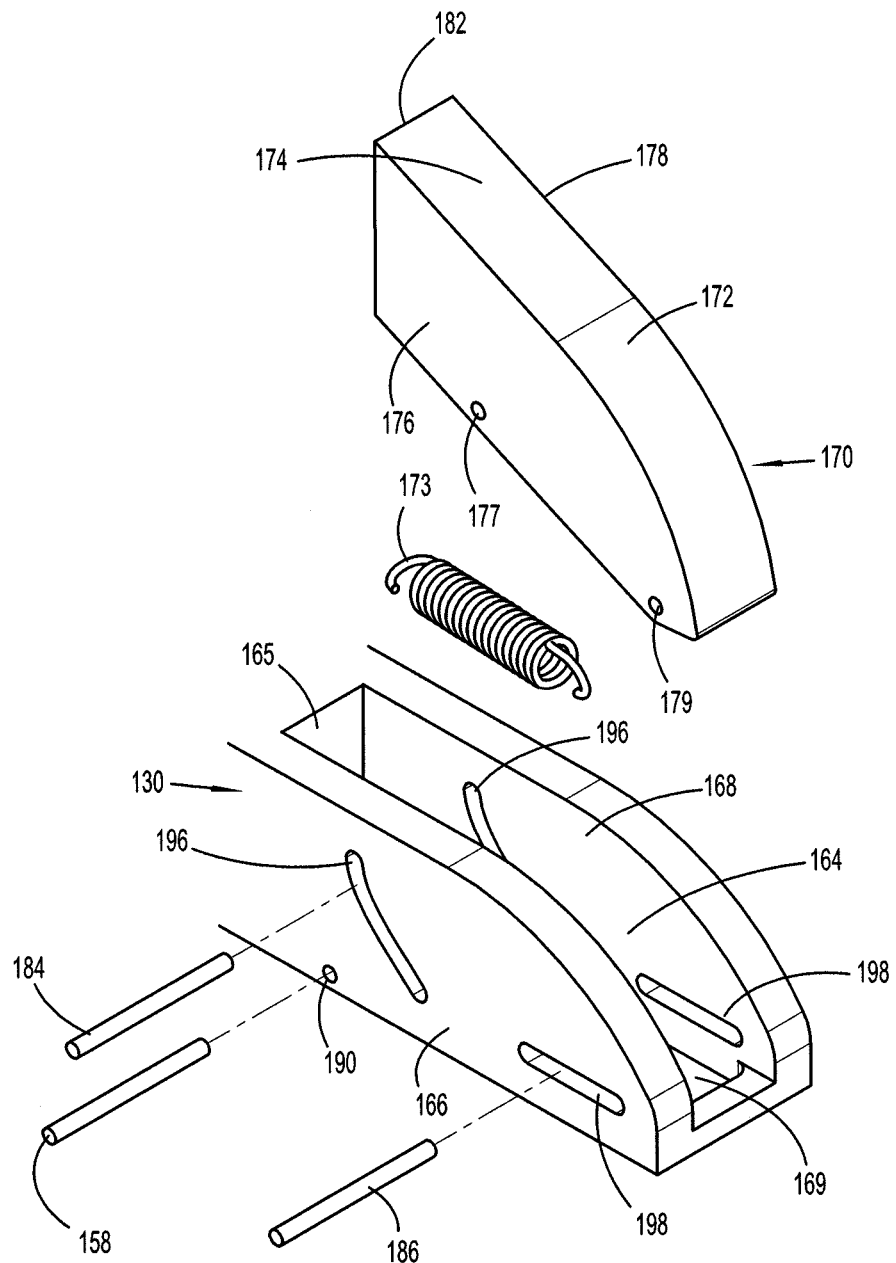
FIG. 4 is a perspective exploded view of a distal portion of a jaw member of the surgical instrument including the tissue stop of FIG. 3.

With reference to FIGS. 3 and 4, tissue stop 170 is movably disposed at least partially within a recess 164 defined in a distal portion of jaw member 130. The term "distal" typically refers to that part or component of the instrument that is farther away from the user. As used herein, the terms "distal" and "proximal" will take into account the curvature of curved parts of the surgical instrument of the present disclosure. For example, "distal" will refer to the portion of the curved part that is farthest from the user, along a trajectory defined by the curved part. That is, while an intermediate portion of a curved part may be farther from the user during use, the portion of the curved part that is farthest along its longitudinal axis is considered "distal."

The distal portion of jaw member 130 defines recess 164 and includes a proximal wall 165, a pair of side walls 166, 168 and a lower surface 169. Tissue stop 170 includes a body 172 having an upper, tissue-contacting surface 174, a pair of lateral walls 176, 178, and a stopping portion 182 configured and adapted to engage tissue (e.g., tissue that is distally directed from between the jaw members).

A pair of camming pins, including a proximal camming pin 184 and a distal camming pin 186, is also disclosed. Each camming pin 184, 186 is configured to extend transversely through both lateral walls 176, 178 of body 172. Proximal camming pin 184 is configured to extend through a first pair of holes 177 of body 172 (only a single hole 177 is shown on lateral wall 176; the hole that is disposed through lateral wall 178 is not visible in FIG. 4), and is configured to engage a pair of proximal cam slots 196, which extend at least partially through each side wall 166, 168 of recess 164. Distal camming pin 186 is configured extend through a second pair of holes 179 of body 172 (only a single hole 179 is shown on lateral wall 176; the hole that is disposed through lateral wall 178 is not visible in FIG. 4), and is configured to engage a pair of distal cam slots 198, which extend at least partially through each side wall 166, 168 of recess 164. As can be appreciated, the engagement between camming pins 184, 186, jaw member 130, and tissue stop 170 movably secure tissue stop 170 to jaw member 130.

In the illustrated embodiments, distal cam slots 198 are substantially parallel to tissue-contacting surface 134 of jaw member 130, and proximal cam slots 196 form an angle with respect to tissue-contacting surface 134 of jaw member 130. It is envisioned that proximal cam slots 196 include at least one curved portion, at least one linear portion, or combinations of at least one curved and at least one linear portion. The illustrated configuration of cam slots 196, 198 allows tissue stopping portion 182 to be movable in and out of recess 164 adjacent proximal wall 165 with a reduced clearance gap "G" therebetween (see FIG. 5). It is also envisioned that gap "G" may be minimized at every moment when tissue stop 170 moves from the first position to the second position. Other cam arrangements can be used to connect the tissue stop to the jaw. The cam can be shaped to maximize the height of the tissue stop when the tissue stop is extended from the jaw (the first position) and/or minimize the space within the jaw occupied by the tissue stop when the tissue stop is in the retracted, second position.

Figure 5:
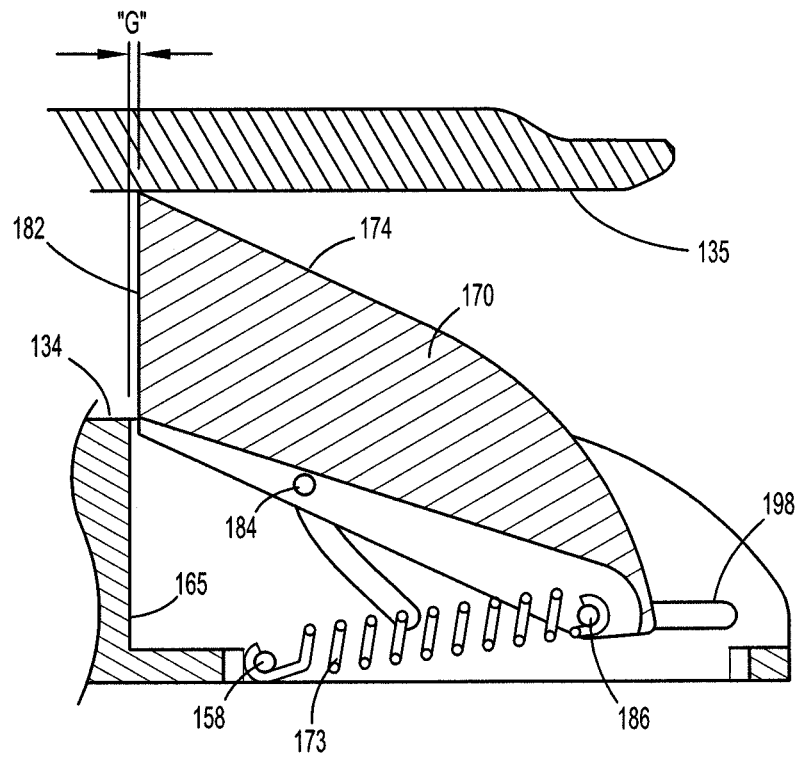
FIG. 5 is a longitudinal cross-sectional view of the tissue stop mechanically engaged with the jaw members of the surgical instrument.

As shown in FIG. 5, tissue stop 170 also includes a biasing member 173. Biasing member 173 is configured to mechanically engage camming pin 186 and to mechanically engage a support pin 158 that extends through an opening 190 (see FIG. 4) on each side wall 166, 168 of jaw member 130. However, it is also contemplated that any other retaining member, such as, for example, a post, may replace support pin 158 to retain one end of biasing member 173. Biasing member 173 urges distal camming pin 186 to its proximal-most position within camming slots 198. In response to the distal camming pin 186 being proximally urged, proximal camming pin 184 is also proximally urged due to the mechanical relationship between camming pins 184, 186, biasing member 173, and tissue stop 170. When camming pins 184, 186 are in their proximal-most positions within caroming slots 196, 198, respectively, tissue stop 170 is located in a first position, in which stopping portion 182 is exposed and extends at least partially out of recess 164, i.e., disposed between tissue-contacting surfaces 134, 135 of cartridge and anvil assemblies 132, 142, respectively (see FIG. 5, for example).

Figure 8:
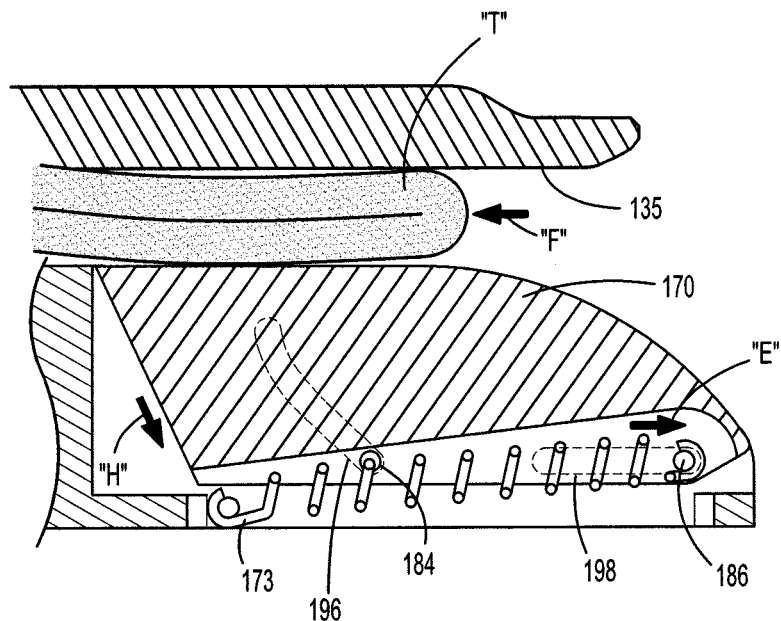

Tissue stop 170 is movable between the first position, as shown in FIG. 5, and a second position, as illustrated in FIG. 8. In the first position which corresponds to when jaw members 130, 140 are in an open position, at least a portion (e.g., a majority, or the entire portion) of stopping portion 182 is exposed out of recess 164. The approximation of the jaw members 130, 140 causes tissue stop 170 to move towards its second position. That is, as one jaw member (e.g., jaw member 140) moves towards the other jaw member (e.g., jaw member 130), tissue-contacting surface 135 contacts tissue-contacting surface 174 of tissue stop 170, and physically urges tissue stop 170 towards its second position against the bias of biasing member 173. In the second position which corresponds to when jaw members 130, 140 are in the approximated position, a majority (e.g., the entirety) of stopping portion 182 is disposed within recess 164. In this embodiment, when tissue stop 170 is disposed in the first position, stopping portion 182 is orthogonally disposed (e.g., substantially perpendicular) relative to tissue-contacting surface 134. As can be appreciated, such an orientation may help impede tissue from distally escaping tool assembly 150. In other embodiments, the instrument can include an actuator that is connected to the tissue stop so that the user can move the tissue stop between the first and second positions by manipulating a button or lever. Such actuator may also include a lock and/or latch for locking the position of the tissue stop.

Figure 6:
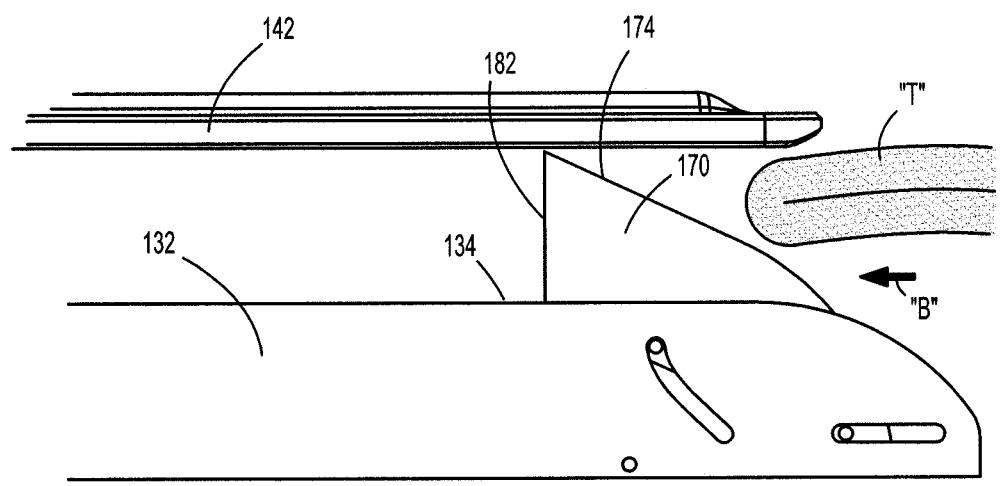
FIG. 6 is a side view of a portion of the jaw members and the tissue stop prior to insertion of tissue.
Figure 7:
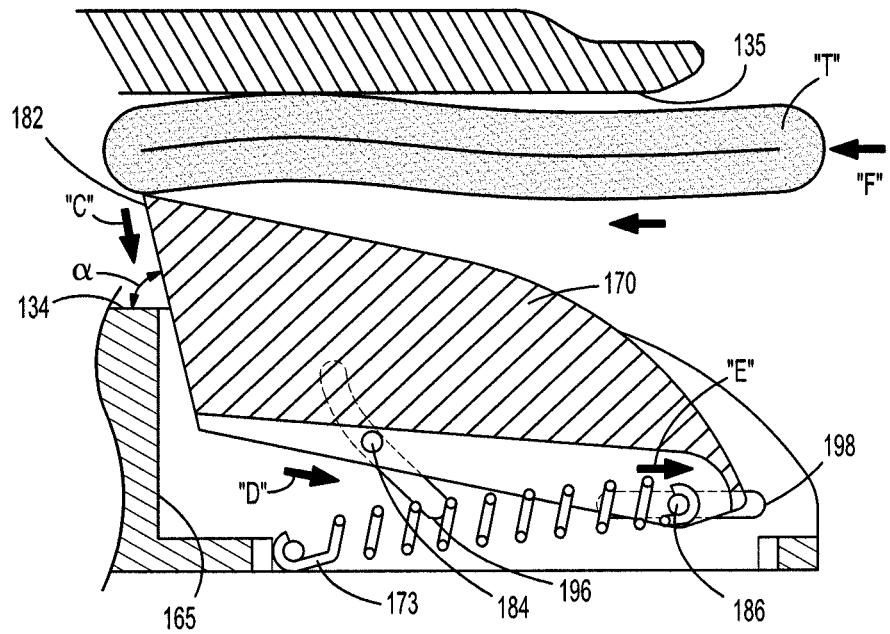
FIGS. 7-9 are longitudinal cross-sectional views of a portion of jaw members and a tissue stop interacting with the tissue at various stages of operation in accordance with another embodiment of the present disclosure.

In use, a surgeon initially positions surgical stapling instrument 100 adjacent a target tissue as shown in FIG. 6. Here, tissue stop 170 is in the first position where the jaw members 130, 140 are in an open position and at least a portion of stopping portion 182 is exposed out of recess 164. Then tissue "T" is introduced into tool assembly 150, between jaw members 130, 140. The angle defined by upper tissue-contacting surface 174 of tissue stop 170 facilitates introduction of tissue "T" into tool assembly 150 in the general direction of arrow "B," as seen in FIG. 6. As tissue "T" is proximally inserted into tool assembly 150, tissue "T" comes into contact with tissue stop 170 and may force at least a portion of stopping portion 182 into recess 164 in the general direction of arrow "C" as shown in FIG. 7. In certain embodiments, the tissue stop has a sloped surface facing the open end of the jaws to encourage the tissue to move the tissue stop. Alternatively, tissue "T" may be proximally inserted between the jaw members 130, 140 by moving in the space between the tissue-contacting surface 135 of jaw member 140 and tissue-contacting surface 174 of tissue stop 170 without necessarily contacting stop member 170.

When moved towards its second position, tissue stopping portion 182 moves in the general direction of arrow "C" (FIG. 7). As tissue stopping portion 182 is translated in the general direction of arrow "C," distal camming pin 186 distally translates along distal camming slot 198 in the general direction of arrow "E" (FIG. 7), while proximal camming pin 184 slides distally along proximal camming slot 184 in the general direction of arrow "D" (FIG. 7).

Figure 9:
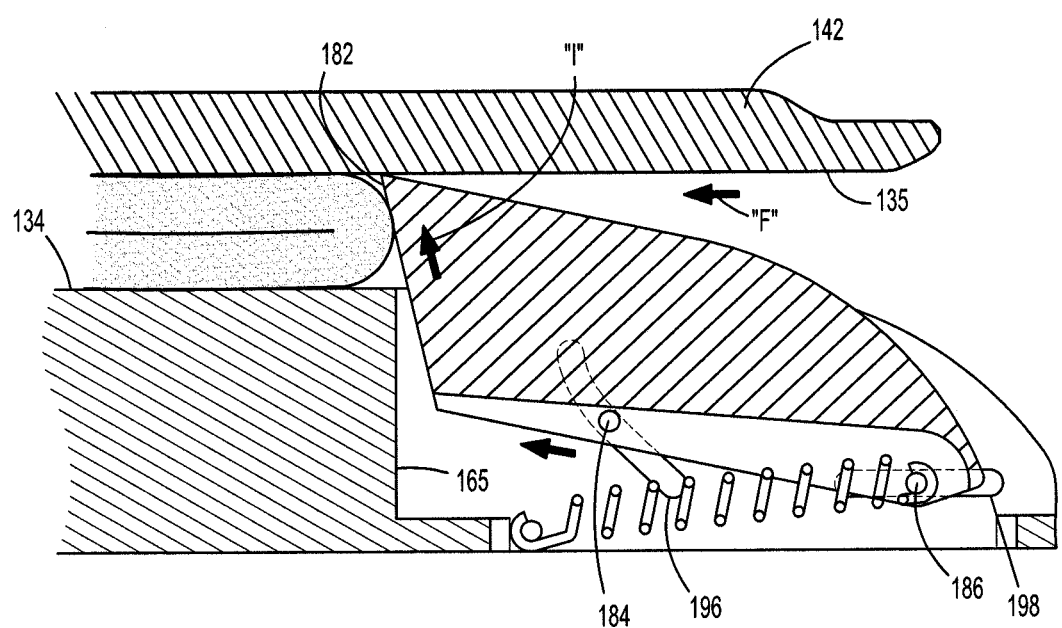

After the surgeon has placed at least a portion of tissue "T" between jaw members 130, 140, the surgeon can actuate an approximation mechanism, e.g., by pivoting movable handle 112 towards stationary handle 114 to approximate anvil assembly 142 towards cartridge assembly 132, to capture tissue "T" between tissue-contacting surfaces 134, 135 as shown in FIG. 8. Here, a proximal portion of tissue-contacting surface 174 of tissue stop 170 is substantially flush with tissue-contacting surface 134 of cartridge assembly 132, and anvil assembly 142 exerts a force against stop member 170 (through tissue "T") toward recess 164. In response to the force exerted by the anvil assembly 142 on tissue stop 170, camming pin 186 translates farther distally along camming slot 198 in the general direction of arrow "E" until the camming pin 186 is in the distal-most portion of camming slot 198. Additionally, camming pin 184 slides farther distally along camming slot 196 in the general direction of arrow "H" (FIG. 8) until camming pin 184 reaches the distal-most portion of camming slot 196, against the bias of biasing member 173. Tissue "T" is now interposed between jaw members 130, 140 and may be pushed farther proximally by surgeon in the general direction of arrow "F" (FIGS. 7-9). As a distal end of tissue "T" is pushed proximally of tissue stop 170 in the general direction of "F," the biasing force exerted by biasing member 173 pushes tissue stop 170 in the general direction of arrow "I," towards (and possibly against) tissue-contacting surface 135 of anvil assembly 142. Here, camming pins 184, 186 have moved proximally along camming slots 196, 198, respectively, proportional to the thickness of tissue "T."

In the embodiment illustrated in FIG. 9, tissue stop 170 is in contact with tissue-contacting surface 135 and is located distally of tissue "T," thereby impeding or preventing any distal escape of tissue "T." At this time, the surgeon may perform a surgical procedure on tissue "T," e.g., staple, seal and/or cut tissue "T." After performing the surgical procedure, jaw member 140 is moved away from jaw member 130, and tissue stop 170 returns to its first position in response to the biasing force.

Figure 10:
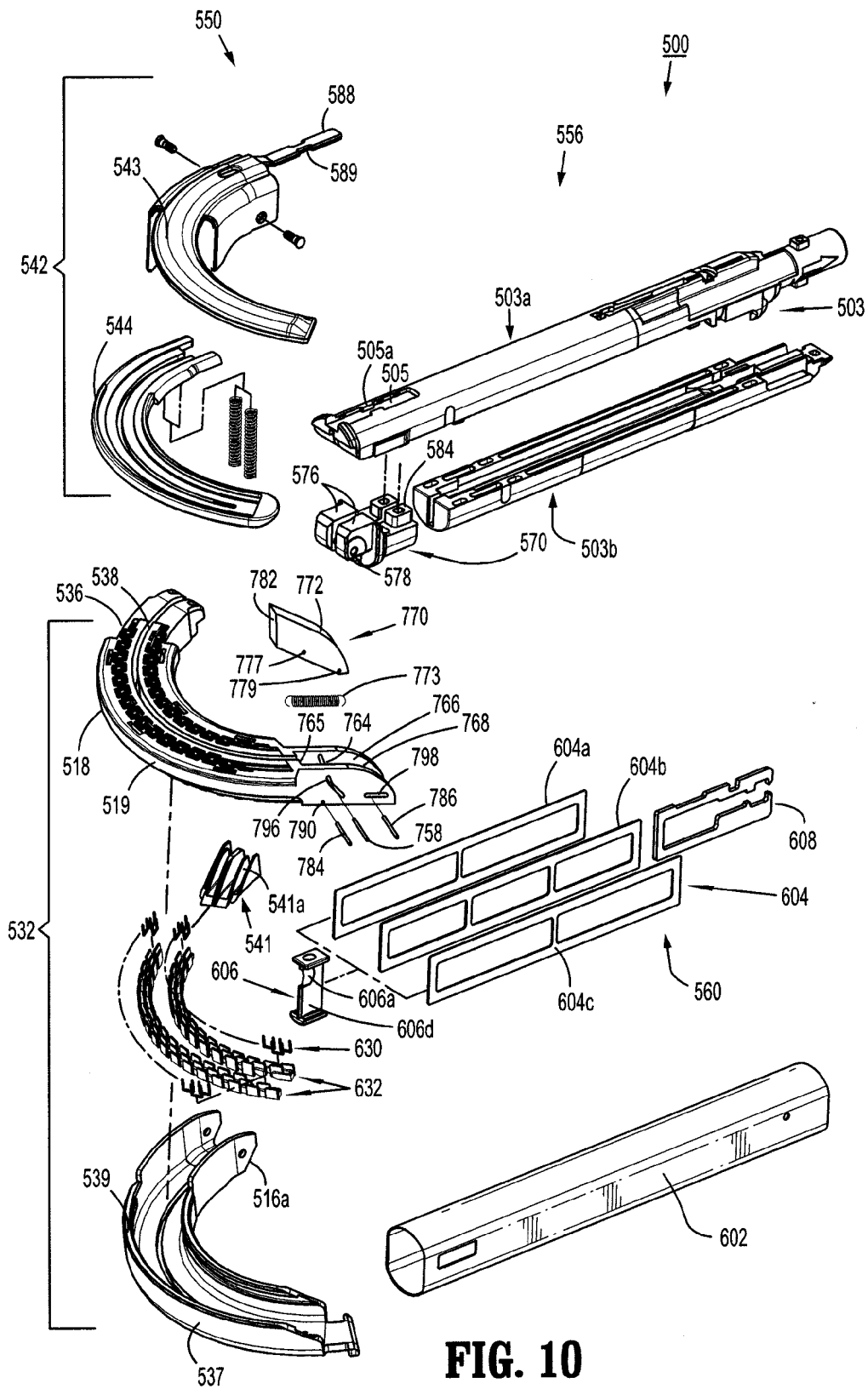
FIG. 10 is a perspective assembly view of a loading unit in accordance with another embodiment of the present disclosure.

With reference to FIG. 10, a loading unit 500 in accordance with another embodiment of the present disclosure is illustrated. Loading unit 500 includes a proximal body portion 556 and a tool assembly 550. Proximal body potion 556 is releasably attachable to a distal end of elongate portion 120. Tool assembly 550 includes a pair of jaw members including an anvil assembly 542 and a cartridge assembly 532. In particular, cartridge assembly 532 is pivotal in relation to anvil assembly and is movable between an open or unclamped position and a closed or approximated position.

Anvil assembly 542 includes a longitudinally curved anvil cover 543 and a longitudinally curved anvil plate 544, which defines a plurality of staple forming depressions. When tool assembly 550 is in the approximated position, staple forming depressions are positioned in juxtaposed alignment with cartridge assembly 532. Cartridge assembly 532 includes a longitudinally curved carrier 537, which receives a longitudinally curved cartridge 518 via, for example, a snap-fit connection. Cartridge 518 includes a pair of support struts 519 which rest on sidewalls 539 of carrier 537 to stabilize cartridge 518 on carrier 537. An external surface of carrier 537 includes an angled cam surface 516a.

Cartridge 518 defines a plurality of laterally spaced staple retention slots 536. Each slot 536 is configured to receive a staple 630 therein. Cartridge 518 includes a central longitudinally curved slot 538. As an actuation sled 541 moves through cartridge 518, cam wedges 541a of actuation sled 541 sequentially engage pushers 632 to move pushers 632 vertically within staple retention slots 536 and eject staples 630 into staple forming depressions of anvil plate 544. Subsequent to the ejection of staples 630 from retention slots 536, a cutting edge 606a of dynamic clamping member 606 severs the stapled tissue as cutting edge 606a travels through curved slot 538 of cartridge 518.

With continued reference to FIG. 10, proximal body portion 556 includes an inner body 503 formed from molded half-sections 503a and 503b and a drive assembly 560. Proximal body portion 556 is coupled to tool assembly 550 by a mounting assembly 570. Mounting assembly 570 has a pair of extensions 576 which extend into a proximal end of carrier 537. Each extension 576 has a transverse bore 578 which is aligned with holes 516A of carrier 539 such that mounting assembly 570 is pivotally secured to cartridge 518 with carrier 539. Mounting assembly 570 is fixedly secured to half-section 503a by a pair of vertical protrusions 584. Vertical protrusions 584 extend upwardly from mounting assembly 570 and frictionally fit into corresponding recesses in half-section 503a.

Anvil cover 543 includes a proximally extending finger 588 having a pair of cutouts 589 formed therein. Cutouts 589 are positioned on each lateral side of finger 588 to help secure anvil cover to half-section 503a. Half-section 503a includes a channel 505 that includes a pair of protrusions 505a. Finger 588 of anvil cover mechanically engages channel 505 of half-section 503a, such that cutouts 589 are aligned with protrusions 505a. An outer sleeve 602 covers the finger 588 and channel 505. The configuration of finger 588 and channel 505 facilitates a secure connection between anvil cover 543 and half-section 503a. Moreover, this connection results in a non-movable (e.g., non-pivotable) anvil assembly 542 with respect to proximal body portion 556.

Drive assembly 560 includes a flexible drive beam 604 which is constructed from three stacked metallic sheets 604a-c and a proximal engagement portion 608. At least a portion of drive beam 604 is sufficiently flexible to be advanced through the curvature of the tool assembly 550. Drive beam 604 has a distal end which is secured to a dynamic clamping member 606. Dynamic clamping member 606 includes a knife or cutting edge 606a at a distal face of vertical strut 606d.

Loading unit 500 includes a tissue stop 770 movably disposed at least partially within a recess 764 defined in a distal portion of cartridge 518. Recess 764 is defined by a proximal wall 765, a pair of side walls 766, 768 and a lower surface. Tissue stop 770 includes a body 772 having an upper, tissue-contacting surface, a pair of lateral walls and a stopping portion 782 configured and adapted to engage tissue. A proximal camming pin 758 and a distal camming pin 786 are each configured to extend transversely through both lateral walls 766, 768 of body 772. Proximal camming pin 758 is configured to extend through a first through hole 777 of body 772, and is configured to engage a pair of proximal cam slots 796, which extend at least partially through each side wall 766, 768. Distal camming pin 786 is configured to extend through a second through hole 779 of body 772, and is configured to engage a pair of distal cam slots 798, which extend at least partially through each side wall 766, 768. It is also contemplated that at least one 796, 798 is only defined in one of the side walls 766, 768.

Tissue stop 770 also includes a biasing member 773. Biasing member 773 is configured to mechanically engage camming pin 786 and to mechanically engage a support pin 784 that extends through an opening 790 (see FIG. 4) on each side wall 766, 768 of cartridge assembly 532. Biasing member 773 urges distal camming pin 786 to its proximal-most position within camming slots 798. In response to the urging of distal camming pin 786 in the proximal direction, proximal camming pin 758 is also proximally urged due to the mechanical relationship between camming pins 758, 786, biasing member 773, and tissue stop 770. When camming pins 758, 786 are in their proximal-most positions within camming slots 796, 798, respectively, stopping portion 782 is exposed and extends at least partially out of recess 764. The operation of loading unit 500 is substantially similar to those described above and will be omitted in the interest of brevity.

Figure 11:
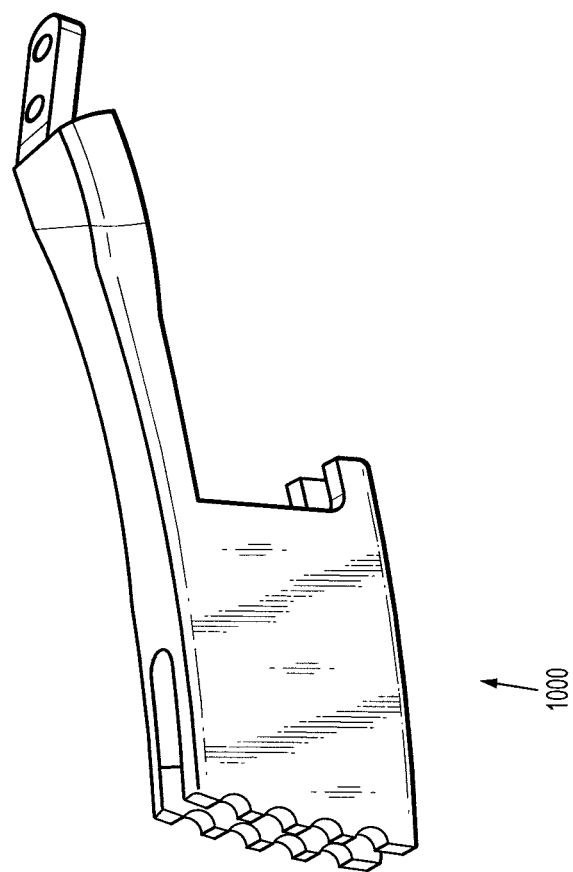
FIGS. 11 and 12 are perspective views of a tissue stop including a stamped metal portion and an overmolded plastic portion for use with the surgical instrument of FIG. 1 in accordance with an embodiment of the present disclosure.
Figure 12:
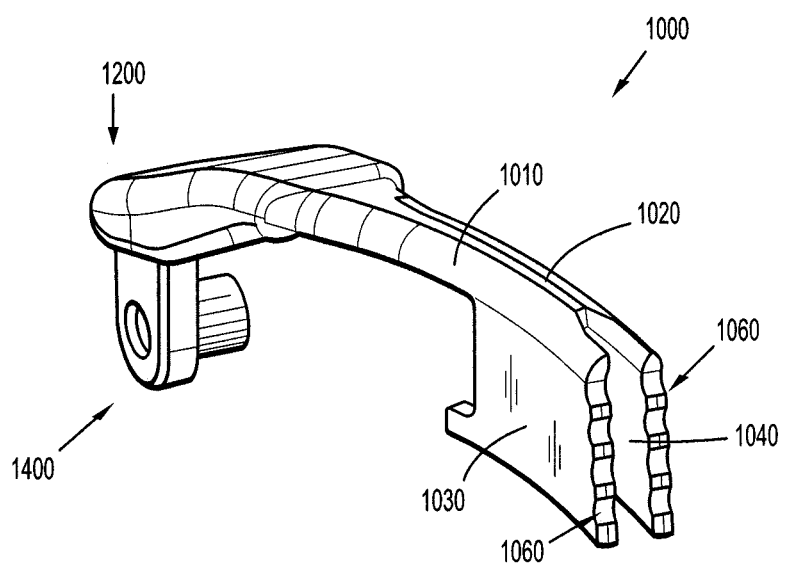
Figure 14:
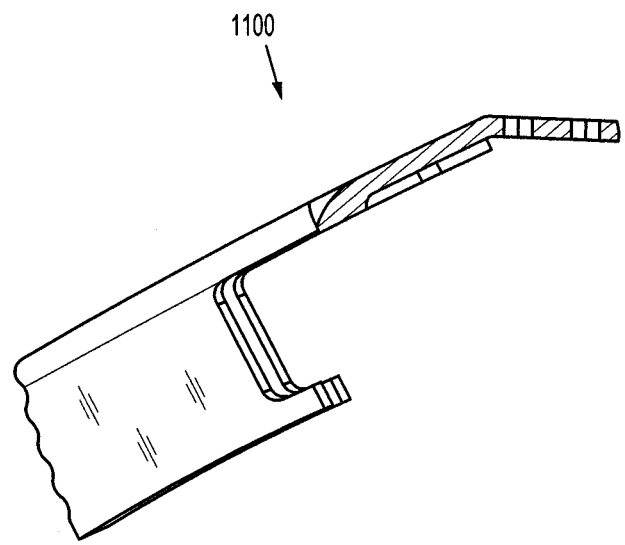
FIGS. 14-17 are various views of the stamped metal portion of the tissue stop of FIGS. 11 and 12.
Figure 13:
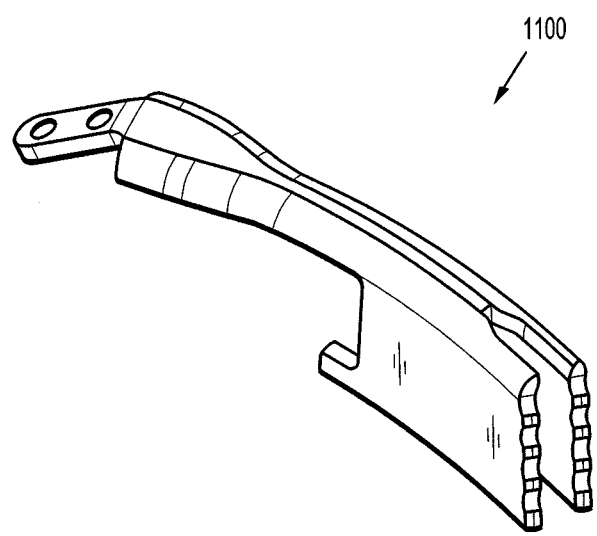
FIG. 13 is a perspective view of a stamped metal portion of the tissue stop of FIGS. 11 and 12.
Figure 15:
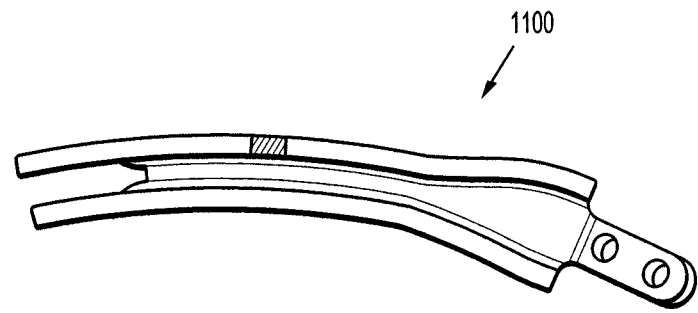
Figure 16:
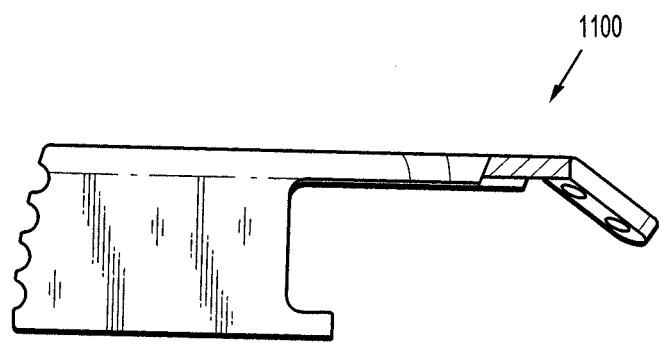
Figure 17:
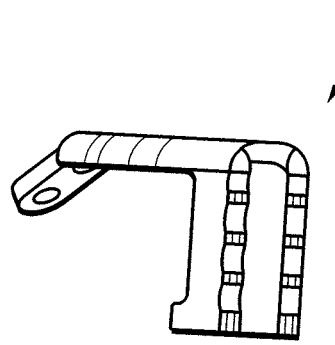

With reference to FIGS. 11-17, a tissue stop 1000 in accordance with an embodiment of the present disclosure is illustrated. Tissue stop 1000 is made of two parts: a stamped metal section 1100 and an overmolded plastic section 1200. The stamped metal section 1100 is illustrated in FIGS. 13-17, and the overmolded plastic section 1200, which at least partially covers the stamped metal section 1100, is illustrated in FIGS. 11-12. The multiple piece design of the tissue stop 1000 provides the strength of the metal while allowing complex geometries that are suitable for plastic injection molding. While particular portions of tissue stop 1000 are shown being made from stamped metal, it is envisioned and within the scope of the present disclosure that the stamped metal portion 1100 can include a greater or lesser portion of the entire tissue stop 1000. Likewise, the overmolded plastic section 1200 may also include a greater or lesser portion of the entire tissue stop 1000 than what is illustrated.

Tissue stop 1000 includes a body 1010 having an upper, tissue-contacting surface 1020, a pair of lateral walls 1030, 1040, and a stopping portion 1050 configured and adapted to engage tissue (e.g., tissue that is distally directed from between the jaw members). Stopping portion 1050 of tissue stop 1000 includes a scalloped portion 1060 including a plurality of spaced-apart semi-circular indents. More specifically, scalloped portion 1060 is disposed on a proximal edge of each lateral wall 1030, 1040. As can be appreciated, scalloped portion 1060 is configured to help prevent tissue from sliding with respect to tissue stop 1000.

Tissue stop 1000 is usable with the camming pins 184, 186, as discussed above with reference to tissue stop 170, and tissue stop 1000 may also include a pivoting protrusion 1400 extending transversely from body 1010, as shown in FIGS. 11 and 12. Pivoting protrusion 1400 is configured to pivotably engage a portion of the cartridge assembly to enable pivotal movement therebetween.

Additionally, in disclosed embodiments, the surgical instrument 100 and loading unit 180 described in connection with FIGS. 1 through 10 includes the stamped/molded tissue stop 1000.

It will be understood that various modifications may be made to the embodiments of the presently disclosed surgical instruments. Therefore, the above description should not be construed as limiting, but merely as exemplifications of embodiments. Those skilled in the art will envision other modifications within the scope and spirit of the present disclosure.

The invention claimed is:

1. A surgical instrument for surgically joining tissue comprising:
    a handle assembly including a movable handle;
    an elongate portion extending distally from the handle assembly and defining a longitudinal axis;
    a pair of opposed jaw members operatively coupled to the elongate portion and extending distally therefrom, the pair of opposed jaw members including a first jaw member and a second jaw member; and
    a tissue stop being mechanically engaged with the first jaw member such that at least a portion of the tissue stop is longitudinally movable along an axis of the first jaw member, the tissue stop being configured to retain tissue between the pair of opposed jaw members, the tissue stop being movable between a first position, where a stopping portion of the tissue stop is disposed between a tissue-contacting surface of the first jaw member and a tissue-contacting surface of the second jaw member, and a second position, where the stopping portion is between the tissue-contacting surface of the first jaw member and a lower surface of the first jaw member, wherein the tissue stop is made of a first part and a second part at least partially covering the first part, the first part including stamped metal and the second part including overmolded plastic.

2. The surgical instrument of claim 1, wherein the stopping portion of the tissue stop includes a scalloped portion.

3. The surgical instrument of claim 2, wherein the scalloped portion of the tissue stop includes a plurality of spaced-apart semi-circular indents.

4. The surgical instrument of claim 1, wherein the tissue stop includes a pair of lateral walls.

5. The surgical instrument of claim 4, wherein the stopping portion is disposed on a proximal edge of each lateral wall.

6. The surgical instrument of claim 5, wherein the stopping portion includes a scalloped portion.

7. The surgical instrument of claim 1, wherein at least a portion of the tissue stop is pivotable relative to the first jaw member.

8. A loading unit configured for releasable engagement with a surgical instrument comprising:
    a body portion defining a longitudinal axis, the body portion including a proximal portion configured for releasable engagement with an elongate portion of the surgical instrument;
    a pair of jaw members extending distally from the body portion, at least one of the jaw members being movable with respect to the other between an open position and an approximated position engaging body tissue therebetween, the pair of jaw members including a first jaw member and a second jaw member; and a tissue stop being mechanically engaged with the first jaw member such that at least a portion of the tissue stop is translatable along an axis of the first jaw member, the tissue stop being configured to retain body tissue between the pair of opposed jaw members, the tissue stop being movable between a first position, where a stopping portion of the tissue stop is disposed between a tissue-contacting surface of the first jaw member and a tissue-contacting surface of the second jaw member, and a second position, where the stopping portion is between the tissue-contacting surface of the first jaw member and a lower surface of the first jaw member, wherein the tissue stop is made of a first part and a second part at least partially covering the first part, the first part including stamped metal and the second part including overmolded plastic.

9. The loading unit of claim 8, wherein the stopping portion of the tissue stop includes a scalloped portion.

10. The loading unit of claim 9, wherein the scalloped portion of the tissue stop includes a plurality of spaced-apart semi-circular indents.

11. The loading unit of claim 8, wherein the tissue stop includes a pair of lateral walls.

12. The loading unit of claim 11, wherein the stopping portion is disposed on a proximal edge of each lateral wall.

13. The loading unit of claim 12, wherein the stopping portion includes a scalloped portion.

14. The loading unit of claim 8, wherein at least a portion of the tissue stop is pivotable relative to the first jaw member.

15. A tissue stop for use with a surgical instrument comprising:
   a first part including stamped metal; and
   a second part at least partially covering the first part, the second part including overmolded plastic;
   wherein the tissue stop is mechanically engaged with a jaw member of the surgical instrument such that at least a portion of the tissue stop is movable along a longitudinal axis of the jaw member, the tissue stop is configured to retain tissue between opposed jaw members of the surgical instrument.

16. The tissue stop of claim 15, wherein the tissue stop includes a pair of lateral walls.

17. The tissue stop of claim 16, wherein a stopping portion is disposed on a proximal edge of each lateral wall.

18. The tissue stop of claim 17, wherein the stopping portion includes a scalloped portion.

19. The tissue stop of claim 18, wherein the scalloped portion of the tissue stop includes a plurality of spaced-apart semi-circular indents.

20. The tissue stop of claim 15, wherein at least a portion of the tissue stop is pivotable relative to the jaw member.

* * * * *